US009724300B2

(12) United States Patent
Yamashita et al.

(10) Patent No.: US 9,724,300 B2
(45) Date of Patent: Aug. 8, 2017

(54) LONG-LASTING, CONTROLLED-RELEASE LOCAL ANESTHETIC LIPOSOME PREPARATION

(71) Applicants:Terumo Kabushiki Kaisha, Shibuya-ku, Tokyo (JP); Kansai Medical University Educational Corporation, Hirakata, Osaka (JP)

(72) Inventors: Keiko Yamashita, Kanagawa (JP); Yasuo Kurosaki, Kanagawa (JP); Makoto Harumoto, Kanagawa (JP); Kyoko Shimamura, Kanagawa (JP); Masaki Kaibori, Osaka (JP); Yoshiro Araki, Osaka (JP); Masanori Kon, Osaka (JP); Seiji Ito, Osaka (JP)

(73) Assignees: TERUMO KABUSHIKI KAISHA, Tokyo (JP); KANSAI MEDICAL UNIVERSITY EDUCATIONAL CORPORATION, Osaka (JP)

( * ) Notice: Subject to any disclaimer, the term of this patent is extended or adjusted under 35 U.S.C. 154(b) by 0 days.

(21) Appl. No.: 14/662,650

(22) Filed: Mar. 19, 2015

(65) Prior Publication Data

US 2015/0250724 A1 Sep. 10, 2015

Related U.S. Application Data

(63) Continuation of application No. PCT/JP2013/075323, filed on Sep. 19, 2013.

(60) Provisional application No. 61/730,633, filed on Nov. 28, 2012.

(30) Foreign Application Priority Data

Sep. 21, 2012 (JP) ................................. 2012-208890
Apr. 1, 2013 (JP) ................................. 2013-076408

(51) Int. Cl.

| *A61K 9/127* | (2006.01) |
| *A61K 31/167* | (2006.01) |
| *A61K 31/445* | (2006.01) |
| *A61K 9/00* | (2006.01) |

(52) U.S. Cl.
CPC ............ *A61K 9/127* (2013.01); *A61K 9/0019* (2013.01); *A61K 9/1278* (2013.01); *A61K 31/167* (2013.01); *A61K 31/445* (2013.01)

(58) Field of Classification Search
CPC .................................................... A61K 9/127
See application file for complete search history.

(56) References Cited

U.S. PATENT DOCUMENTS

| 4,687,661 | A | | 8/1987 | Kikuchi et al. | |
| 5,089,181 | A | * | 2/1992 | Hauser ................... | A61K 9/127 264/4.1 |
| 5,192,549 | A | | 3/1993 | Barenolz et al. | |
| 5,244,678 | A | * | 9/1993 | Legros .................... | A61K 9/127 424/450 |
| 6,162,462 | A | * | 12/2000 | Bolotin ................ | A61K 31/445 264/4.1 |
| 8,182,835 | B2 | * | 5/2012 | Kim ...................... | A61K 9/0019 424/450 |
| 2004/0142025 | A1 | | 7/2004 | MacLachlan et al. | |
| 2004/0156891 | A1 | | 8/2004 | Bolotin et al. | |
| 2006/0078606 | A1 | * | 4/2006 | Kim et al. .................... | 424/450 |
| 2009/0041833 | A1 | | 2/2009 | Bettinger et al. | |
| 2009/0041835 | A1 | | 2/2009 | Kato et al. | |
| 2010/0021531 | A1 | | 1/2010 | Yoshino et al. | |
| 2011/0183954 | A1 | | 7/2011 | Almeida et al. | |
| 2013/0202686 | A1 | | 8/2013 | Yamashita et al. | |

(Continued)

FOREIGN PATENT DOCUMENTS

| JP | 60-7932 A | 1/1985 |
| JP | 6-239734 A | 8/1994 |
| JP | 2659136 B2 | 9/1997 |

(Continued)

OTHER PUBLICATIONS

International Search Report (PCT/ISA/210) mailed on Dec. 10, 2013, by the Japanese Patent Office as the International Searching Authority for International Application No. PCT/JP2013/075323.

Grant, G.J. et al., A novel liposomal bupivacalne formulation to produce ultralong-acting analgesia, Anesthesiology, Jul. 2004, vol. 101, No. 1, pp. 133-137.

Elyad M. Davidson et al., High-Dose Bupivacaine Remotely Loaded into Multivesicular Liposomes Demonstrates Slow Drug Release Without Systemic Toxic Plasma Concentrations After Subcutaneous Administration in Humans, www.anesthesia-analgesia.org, Apr. 2010, vol. 110, No. 4, pp. 1018-1023.

(Continued)

*Primary Examiner* — Frederick Krass
*Assistant Examiner* — Amanda Heyes
(74) *Attorney, Agent, or Firm* — Buchanan, Ingersoll & Rooney PC

(57) ABSTRACT

A long-lasting, controlled-release local anesthetic liposome preparation is produced by: providing a liposome composition, which is obtained by mixing, in a water-miscible organic solvent, a first aqueous phase solution with a water-miscible organic solution, in which a phospholipid and cholesterol are contained at a defined total concentration, at a defined ratio by volume thereby obtaining an emulsion wherein a total concentration of the phospholipid and cholesterol in the mixed phase is at 15 w/v % to 50 w/v %, followed by subjecting the emulsion to external solution exchange with a second aqueous phase solution to obtain a liposome composition wherein an ion gradient is formed between an internal-region aqueous phase of a liposome membrane made of the first aqueous phase solution and an external-region aqueous phase of the liposome membrane made of the second aqueous phase solution; and encapsulating a local anesthetic in the internal-region aqueous phase according to a remote loading method.

23 Claims, 8 Drawing Sheets

(56) References Cited

U.S. PATENT DOCUMENTS

| | | |
|---|---|---|
| 2013/0309297 A1 | 11/2013 | Yamashita et al. |
| 2014/0004173 A1 | 1/2014 | Hartounian et al. |

FOREIGN PATENT DOCUMENTS

| | | |
|---|---|---|
| JP | 2847065 B2 | 1/1999 |
| JP | 2001/522870 A | 11/2001 |
| JP | 2002/522470 A | 7/2002 |
| JP | 2005-538967 A | 12/2005 |
| JP | 2008-106001 A | 5/2008 |
| JP | 2008-538367 A | 10/2008 |
| JP | 2009-513621 A | 4/2009 |
| JP | 2009-132629 A | 6/2009 |
| JP | 2011-522870 A | 8/2011 |
| WO | 86-01102 A1 | 2/1986 |
| WO | WO 99/25319 A1 | 5/1999 |
| WO | WO 00/09089 A1 | 2/2000 |
| WO | WO 01/00173 A1 | 1/2001 |
| WO | 2004-002453 A1 | 1/2004 |
| WO | WO 2007/049278 A2 | 5/2007 |
| WO | WO 2007049278 A2 * | 5/2007 ............ A61K 9/127 |
| WO | 2009-150462 A1 | 12/2009 |
| WO | WO 2012/091054 A1 | 7/2012 |
| WO | WO 2012/133121 A1 | 10/2012 |

OTHER PUBLICATIONS

E. Davisson et al., "High-Dose Bupivacaine Remotely Loaded into Multivesicular Liposomes Demonstrates Slow Drug Release Without Systemic Toxic Plasma Concentrations After Subcutaneous Administration in Humans", Anesthetic Pharmocology and Preclinical Pharmacology, Apr. 2010, pp. 1018-1023, vol. 110, No. 4.

G. Grant et al., "A Novel Liposomal Bupivacaine Formulation to Produce Ultralong-Acting Analgesia", Anesthesiology, Jul. 2004, pp. 133-137, vol. 101, No. 1.

Haran et al., "Transmembrane Ammonium Sulfate Gradients in Liposomes Produce Efficient and Stable Entrapment of Amphipathic Weak Bases", Biochimica et Biophysica Acta (BBA), Sep. 19, 1993, pp. 201-215; vol. 1151, No. 2, XP023352276.

* cited by examiner

LONG-LASTING, CONTROLLED-RELEASE LOCAL ANESTHETIC LIPOSOME PREPARATION

CROSS-REFERENCES TO RELATED APPLICATIONS

This application is a continuation of International Application No. PCT/JP2013/075323 filed on Sep. 19, 2013, designating the U.S. and claims priority to Japanese Application No. 2012-208890 filed on Sep. 21, 2012, U.S. Ser. No. 61/730,633 filed Nov. 28, 2012 and Japanese Application No. 2013-076408 filed Apr. 1, 2013, the entire content of which is incorporated herein by reference.

TECHNICAL FIELD

Disclosed is a long-lasting, controlled-release liposome preparation containing a local anesthetic.

BACKGROUND DISCUSSION

In recent years, as a consequence of an aging society, there has been an increase in the number of patients needing a care giver, such as patients who suffer from dementia, brain diseases, Parkinson's disease and the like. Such patients may forget to take their own medicine, or may have difficulty in taking medicine because of difficulty in swallowing. Thus, it is difficult for those patients to manage the medicine-taking activity by themselves. Therefore, there is a demand for administrating methods other than peroral administration. Besides, with patients who are treated with anti-mental illness medicine, if their medicine stops working, symptoms appear immediately thereby obstructing their life. To avoid this, administration has to be repeated several times a day before the medicinal efficacy is lost. Frequent administration imposes a great burden on the patient. In view of the above, long-lasting, controlled-release preparations are highly desirable in all disease regions.

For the long-lasting, controlled-release preparation, there have been heretofore investigated preparations for subcutaneous administration or intramuscular administration, most of which are in the form of microspheres making use of polylactic acid-glycolic acid copolymer (PLGA). For instance, mention is made of a microcapsule preparation Leuplin (registered trademark) wherein leuprorelin serving as an anticancer is encapsulated in a crosslinked matrix of PLGA. It is known that with these microspheres based on PLGA, the drug is released immediately after administration (initial burst) and that the concentration of the drug in the blood quickly exceeds an effective concentration, thus raising concerns with side effects. In the case of using PLGA, a difficulty is involved in encapsulating a drug at a high concentration with a high efficiency. Additionally, a limitation is placed on a clinically administrable drug dosage, thus presenting a problem on an improvement in the amount of drug to be encapsulated. Moreover, in the case where PLGA is used, an organic solvent should be used in the course of the preparation step, in which the removal of the organic solvent from the resulting preparation is essential, and which will be often difficult to achieve in the manufacture on an industrial scale. In addition, it has been accepted that the use of PLGA results in an increase in local acidity associated with hydrolysis, which can cause a serious problem in that inflammation occurs in administration site.

Besides, some approaches have been made in which bupivacaine is encapsulated in a multilayer membrane liposome according to a remote loading method. In the document, no relationship between the particle diameter and the controlled-release properties has been disclosed, and no knowledge has been obtained of an optimum particle diameter in controlled-release preparations. In addition, the sustained release time disclosed therein cannot be said to be long-lasting, during which postoperative intense pain continuing over three to five days is enabled to be alleviated for a sufficient period of time. Thus, a problem is presented concerning the duration (Non-Patent Document 1, Non-Patent Document 2, and Patent Document 1). Moreover, a multivesicular liposome (MVL) has been developed as a lipid-based controlled-release drug carrier for local or systematic drug delivery (Patent Document 2). This does not yet ensure a satisfactory duration on a clinical basis, thus presenting a problem.

Patent Document 1: JP-T-2002-522470
Patent Document 2: JP-T-2001-522870
Non-Patent Document 1: Anesthesiology, 2004, Vol. 101, No. 1, pp. 133-137, by Gilbert J. Grant et al., entitled "A Novel Liposomal Bupivacaine Formulation to Produce Ultralong-Acting Analgesia"
Non-Patent Document 2: Anesthesia & Analgesia, 2010, Vol. 110, No. 4, pp. 1018-1023, by Elyad M. Davidson et al., entitled "High-Dose Bupivacaine Remotely Loaded into Multivesicular Liposomes Demonstrates Slow Drug Release Without Systemic Toxic Plasma Concentrations After Subcutaneous Administration in Humans"

SUMMARY

According to one aspect, disclosed is a long-lasting, controlled-release local anesthetic liposome preparation wherein the liposome preparation carrying a local anesthetic is able to maintain an effective drug concentration at an affected site over a long period of time along with an excellent long-lasting analgesic effect.

It has been determined that when a local anesthetic is encapsulated in a liposome composition having an internal aqueous phase that exists uniformly in a multilayer membrane having ten or more layers and an average particle diameter (average maximum outer diameter) is not less than 1 μm wherein an ion gradient is formed between the internal aqueous phase and an external aqueous phase of a liposome (which may be sometimes called empty liposome hereinafter), there can be obtained a liposome preparation having long-lasting, controlled-release properties of the local anesthetic.

Disclosed are the following illustrative aspects.

(1) A long-lasting, controlled-release local anesthetic liposome preparation, which is prepared by: providing a liposome composition obtained by mixing, in a water-miscible organic solvent, a first aqueous phase solution with a water-miscible organic solution, in which a phospholipid and cholesterol are contained at a total concentration of 100 w/v % to 200 w/v %, at a ratio by volume of 3/1 to 12/1 in terms of the unit volume to the water-miscible organic solution thereby obtaining an emulsion wherein a total concentration of the phospholipid and cholesterol in the mixed phase is at 15 w/v % to 50 w/v %, followed by subjecting the emulsion to external solution exchange with a second aqueous phase solution to obtain a liposome composition wherein an ion gradient (ion concentration gradient) is formed between an internal-region aqueous phase of a liposome membrane made of the first aqueous phase solution and an external-region aqueous phase of the liposome membrane made of the second aqueous phase solution; and encapsulating a local anesthetic in the internal-region aqueous phase according to a remote loading method.

(2) The long-lasting, controlled-release local anesthetic liposome preparation as recited in (1) above, wherein the ion gradient is a proton gradient (proton concentration gradient) and a pH of the internal-region aqueous phase of the liposome is lower than a pH of the external-region aqueous phase of the liposome.

(3) The long-lasting, controlled-release local anesthetic liposome preparation as recited in (1) or (2) above, wherein the local anesthetic is retained in the liposome at not less than 0.08 (mol)/total lipids (mol).

(4) The long-lasting, controlled-release local anesthetic liposome preparation as recited in any one of (1) to (3), wherein the liposome has an average particle diameter (average maximum outer diameter) of not less than 1 μm and has the internal-region aqueous phase in a multilayer membrane having ten or more layers.

(5) The long-lasting, controlled-release local anesthetic liposome preparation as recited in any one of (1) to (4), which is used for delivery at an operative wound area and/or an adjacent site thereof, or a nerve periphery transmitting pain according to at least one of methods selected from the group consisting of injection, infiltration and embedment.

(6) The long-lasting, controlled-release local anesthetic liposome preparation as recited in any one of (1) to (4), which is administered in at least one manner selected from the group consisting of subcutaneous, myofascial and intramuscular manners over an operative wound area and/or an adjacent site thereof, or a nerve periphery transmitting pain.

(7) The long-lasting, controlled-release local anesthetic liposome preparation as recited in any one of (1) to (6), which brings about an analgesic duration at least for not less than three days after the administration.

(8) The long-lasting, controlled-release local anesthetic liposome preparation as recited in any one of (1) to (7), wherein the local anesthetic is at least one amino amide-type anesthetic selected from the group consisting of bupivacaine, ropivacaine, levobupivacaine, lidocaine, mepivacaine, prilocaine and salts thereof.

(9) The long-lasting, controlled-release local anesthetic liposome preparation as recited in any one of (1) to (8), which is able to be administered by an injector having an injection needle having at least one gauge size selected from among 27 gauge to 34 gauge.

(10) A kit for a long-lasting, controlled-release local anesthetic liposome preparation, which comprises the long-lasting, controlled-release local anesthetic preparation recited in (9) above and an injector having an injection needle having at least one gauge size selected from among 27 gauge to 34 gauge.

(11) A method for locally anesthetizing a human, the method comprising the step of administering, to a human, the long-lasting, controlled-release local anesthetic liposome preparation recited in any one of (1) to (9).

The disclosed long-lasting, controlled-release local anesthetic liposome preparation can provide excellent persistence. Accordingly, the disclosed long-lasting, controlled-release local anesthetic liposome preparation is able to alleviate post-operative pain over an adequate period of time.

DETAILED DESCRIPTION

Figure 1:
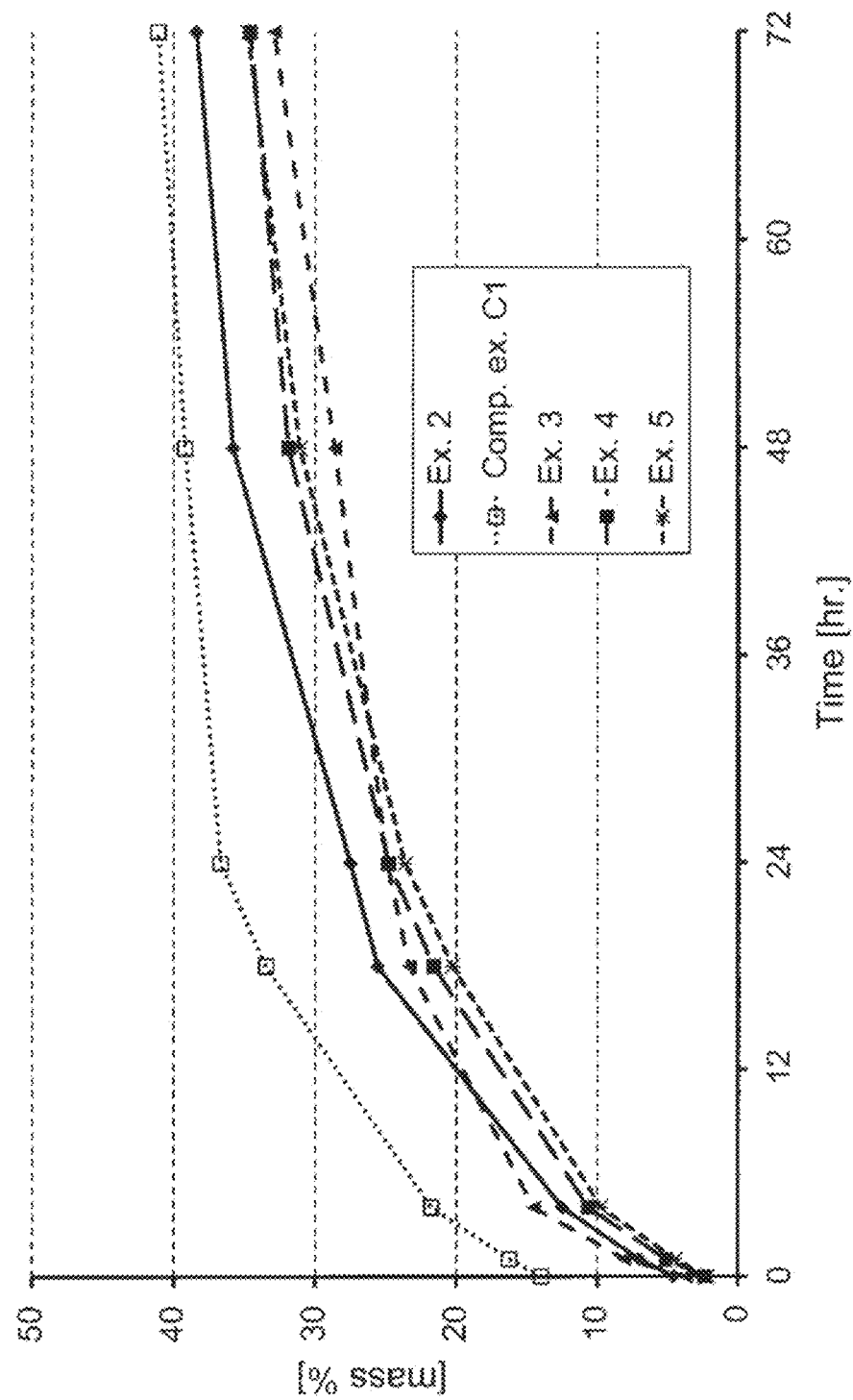
FIG. 1 is a graph showing a timewise change in release rate (%) of ropivacaine hydrochloride from ropivacaine hydrochloride-containing, controlled-release preparations of Examples 2 to 5 and a ropivacaine hydrochloride-containing preparation of Comparative Example C1 prepared according to an existing method.

An illustrative long-lasting, controlled-release local anesthetic liposome preparation is one, which is obtained by mixing, in a water-miscible organic solvent, a first aqueous phase solution with a water-miscible organic solution containing a phospholipid and cholesterol at a total concentration of 100 w/v % to 200 w/v % at a ratio by volume of 3/1 to 12/1 in terms of the unit volume to the water-miscible organic solution to obtain an emulsion wherein a total concentration of the phospholipid and cholesterol in the mixed phase is at 15 w/v % to 50 w/v %, subjecting the emulsion to external solution exchange with a second aqueous phase solution to obtain a liposome composition wherein an ion gradient (ion concentration gradient) is formed between the internal-region aqueous phase of a liposome membrane made of the first aqueous phase solution and an external-region aqueous phase of the liposome membrane made of the second aqueous phase, and encapsulating a local anesthetic in the internal-region aqueous phase by use of a remote loading method.

The disclosed long-lasting, controlled-release local anesthetic liposome preparation remains at an affected site being administered and enables the local anesthetic to be persistently, slowly released at the administration site. Thus, postoperative or the like pain can be alleviated safely without side effects over an adequate period of time.

In accordance with the disclosed embodiments, to enable persistent, slow release of a local anesthetic is referred to as excellence in persistence. In this specification, a composition prior to introduction of a local anesthetic thereinto is referred to as "liposome composition," and a liposome composition after introduction of a local anesthetic into the internal region is referred to as "long-lasting, controlled-release local anesthetic liposome preparation."

The average particle diameter (average maximum outer diameter) of the liposomes of the long-lasting, controlled-release local anesthetic liposome preparation is preferably not less than 1 μm, more preferably 1 μm to 12 μm, much more preferably 2.5 μm to 10 μm, further more preferably 3 μm to 10 μm and much further more preferably 6 μm to 10 μm. The average particle diameter (average maximum outer diameter) of the liposomes can be measured by use of a size distributor, preferably a light-scattering diffraction size distributor. For instance, mention is made of LS 230, made by Beckman Coulter, Inc.

The liposome is such that the walls thereof are constituted of a lipid bilayer membrane. If one layer structure (lamellarity) is formed of one lipid bilayer membrane, the liposome used for the long-lasting, controlled-release local anesthetic liposome preparation should preferably have an outer shell serving as a wall, which is made of a layer structure of ten or more (fold) layers. The number of the layers is such that a layer structure having ten layers to 35 layers (ten to 35-fold layer) is preferred (in which an average particle diameter of such a layer structure is 1 μm to 12 μm), a layer structure having 12 layers to 35 layers (12 to 35-fold layer) is more preferred (wherein an average particle diameter of the layer structure is 2.5 μm to 12 μm), and a layer structure having 13 layers to 27 layers (13 to 27-fold layer) is much more preferred (wherein an average size of the layer structure is 3 μm to 10 μm). These layer structures are ones wherein adjacent outer and inner layer structures exist as substantially contacting each other, and only a small amount of water is present therebetween. The number of the layer structures can be determined by taking a transmission electron microphotograph (TEM) under conditions where part of the walls of the liposome is broken off, and measuring the number of the layer structures.

The liposome used for the liposome preparation has an internal aqueous phase in the inside thereof. The internal aqueous phase is constituted at an internal region of an inner surface of a layer structure that exists at the innermost side. The thickness of one layer structure (lipid bilayer membrane) is at about 10 nm, and if the number of existing lipid bilayer membranes increases, the wall thickness of the liposome increases. Where the layer structure of the lipid bilayer membranes is formed of 20 layers, 10 nm thick 20 layers are arranged at opposite sides of the internal aqueous phase and thus, it is assumed that a thickness of about 0.2 μm is established at one side. When the two-side thickness of about 0.4 μm is subtracted from the outer diameter of the liposome formed of the 20 layers, an approximate diameter of the internal aqueous phase (an inner diameter of liposome) can be calculated.

The diameter of the internal aqueous phase of the liposome preparation is preferably not less than 0.8 μm (ten layers at an average particle diameter of 1 μm), more preferably 2.3 μm (12 layers at an average particle diameter of 2.5 μm) to 11.3 μm (35 layers at an average particle diameter of 12 μm), and much more preferably 2.7 μm (13 layers at an average particle diameter of 3 μm) to 9.5 μm (27 layers at an average particle diameter of 10 μm).

It can be assumed that when the liposome used in the liposome preparation has an average particles size, for example, of 1 μm, the layer structure is formed of ten layers. Likewise, it can also be assumed that when the average particle diameter is, for example, 2.5 μm, the layer structure is formed of 12 layers, when the average particle diameter is 3 μm, the layer structure is formed of 13 layers, when the average particle diameter is 10 μm, the layer structure is formed of 27 layers, and when the average particle diameter is 12 μm, the layer structure is formed of 35 layers. In this regard, however, the liposomes used in the liposome preparation are not limited thereto.

The average particle diameter of the liposomes used in the long-lasting, controlled-release local anesthetic liposome preparation should preferably be not less than 1 urn in view of excellent controlled-release properties and inhibition of liposomes from being diffused from an administration site thereby enabling the liposomes to remain at the administration site without moving into blood vessels. Additionally, this enables ready administration even with a fine needle (e.g., 27 gauge to 34 gauge) and thus, pain can be alleviated. The liposomes prepared in this way ensure favorable controlled-release properties and are able to provide a uniform liposome composition, so that a homogeneous liposome preparation can be produced. This preparation is suited for administration with at least one method selected from the group consisting of injection, infiltration, application and embedment. It will be noted that injection includes local injection, and local infiltration and local application are also included for infiltration and application.

The disclosed long-lasting, controlled-release local anesthetic liposome preparation can be prepared by forming a liposome composition according to the following procedure and further encapsulating a local anesthetic in an internal aqueous phase of liposomes.

Liposome Composition

The liposome composition used for a liposome preparation wherein a local anesthetic is encapsulated is one which is obtained by mixing, in a water-miscible organic solvent, a first aqueous phase solution with a water-miscible organic solution, which contains a phospholipid and cholesterol at a total concentration of 100 w/v % to 200 w/v %, at a ratio by volume of 3/1 to 12/1 in terms of the unit volume to the water-miscible organic solution to obtain an emulsion wherein a total concentration of the phospholipid and cholesterol in the mixed phase is at 15 w/v % to 50 w/v %, and subjecting the emulsion to external solution exchange with a second aqueous phase solution to obtain a liposome composition wherein an ion gradient (ion concentration gradient) is formed between the internal-region aqueous phase of a liposome membrane made of the first aqueous phase solution and an external-region aqueous phase of the liposome membrane made of the second aqueous phase.

The "water-miscible organic solvent" used herein means an alcohol such as methanol, ethanol, isopropyl alcohol, butanol or the like, of which ethanol is preferred.

The "water-miscible organic solution (which may be sometimes referred to alcohol solution hereinafter)" means a solution wherein a phospholipid and cholesterol are contained in an alcohol at a total concentration of 100 w/v % to 200 w/v % (100 g to 200 g in 100 mL).

The "mixed phase" means a mixed phase obtained by mixing a first aqueous phase solution with a water-miscible organic solution at a ratio by volume of 3/1 to 12/1 in terms of the ratio to the unit volume of the water-miscible organic solution wherein a total lipid concentration is at 15 w/v % to 50 w/v % (15 g to 50 g in 100 mL).

The "first aqueous phase" may also be called an internal-region aqueous phase or internal aqueous phase and means an internal-region aqueous phase that exists uniformly in the multilayer membrane of the liposome.

The "second aqueous phase" may also be called an external-region aqueous phase or external aqueous phase and means an aqueous phase that exists outside of the multilayer membrane of the liposome and forms an ion gradient with the internal-region aqueous phase.

Now, individual components are described below.

Phospholipid

The phospholipid is one of the main constituent components of the lipid membrane of the liposome composition for the long-lasting, controlled-release local anesthetic liposome preparation and thus, serves as a main constituent component of a biomembrane. In general, the phospholipid is an amphipathic substance having, in the molecule, both a hydrophobic group made up of a long-chain alkyl group and a hydrophilic group formed of a phosphate group. Preferably, the phospholipids include: glycerophosphoric acids such as phosphatidylcholine (=lecithin), phosphatidylglycerol, phosphatidic acid, phosphatidylethanolamine, phosphatidylserine, phosphatidylinositol and the like; sphingophospholipids such as sphingomyelin (SM) and the like; natural or synthetic diphosphatidylphospholipids such as cardiolipin and the like, and derivatives thereof; hydrogenated products of these phospholipids such as, for example, hydrogenated soybean phosphatidylcholine (HSPC), hydrogenated yolk phosphatidylcholine, distearoylphosphatidylcholine, dipalmitoylphosphatidylcholine and dimyristoylphosphatidylcholine. The phospholipids may be used singly or in combination of a plurality thereof.

Additives Other than Phospholipid

The liposome membrane lipid of the liposome preparation may further contain other types of membrane components along with the above main constituent component. For instance, lipids other than the phospholipids and/or derivatives thereof, antioxidants and the like may be contained as other membrane component, if desired.

So far as the lipids other than phospholipids have a hydrophobic group such as a long-chain alkyl group or the like in the molecule and no phosphate group is contained in the molecule, no specific limitation is placed thereon. Specific examples of lipids other than phospholipids include glyceroglycolipids, sphingoglycolipids, sterol derivatives such as cholesterol, and hydrogenated products and other types of derivatives thereof. As a preferred sterol derivative, mention is made of cholesterols having a cyclopentanohydrophenanthrene ring. The liposome composition should typically contain cholesterol as a lipid other than a phospholipid. A total of a phospholipid and cholesterol may be sometimes indicated as a total lipid.

For the antioxidant, mention is made of ascorbic acid, uric acid, a tocopherol analog, i.e., vitamin E and the like. Although tocopherol includes four isomers of $\alpha$, $\beta$, $\gamma$ and $\delta$-tocopherols, all the isomers can be used without limitation.

It will be noted that the long-lasting, controlled-release local anesthetic liposome composition can be preferably made by choosing a composition of the total lipid of a phospholipid and cholesterol in the following way.

1) The liposome lipid membrane is formed only of a phospholipid having an acyl chain of a saturated fatty acid having a chain length of 16 to 18.

2) In the case where the liposome lipid membrane contains, as its main constituent components, a phospholipid having an acyl chain of a saturated fatty acid having a chain length of 14 to 18 and cholesterol, the molar ratio of both components is at 80:20 to 50:50.

3) In the case where the liposome lipid membrane contains, as its main constituent components, a phospholipid having an acyl chain of an unsaturated fatty acid having a chain length of 16 to 18 and cholesterol, the molar ratio of both components is at 60:40 to 50:50.

The chain length of the acyl chain means the number of carbon atoms of the acyl chain. Individually, myristic acid is mentioned as a saturated fatty acid whose acyl chain has 14 carbon atoms, pentadecylic acid is mentioned as a saturated fatty acid whose acyl chain has 15 carbon atoms, palmitic acid (trivial name: cetylic acid or hexadecylic acid, systematic name: hexadecanoic acid) is mentioned as a saturated fatty acid whose acyl chain has 16 carbon atoms, heptadecanoic acid is mentioned as a saturated fatty acid whose acyl chain has 17 carbon atoms, and each of stearic acid (systematic name: octadecanoic acid), oleic acid, linoleic acid and linoleic acid are mentioned as saturated or unsaturated acids whose acyl chain has 18 carbon atoms.

Liposome Internal Aqueous Phase (First Aqueous Phase) Solution

The internal aqueous phase solution of liposomes used for encapsulating an amphipathic, weakly basic drug in the liposome stably in a high efficiency has an importance on the selection of a counter ion that is encapsulated in the liposome along with the amphipathic, weakly basic drug. The liposome composition can preferably contain a sulfate ion in order to achieve high-efficient encapsulation of a drug and long-lasting, controlled-release properties. For a compound capable of generating a sulfate ion, mention is made of ammonium sulfate, in general. In addition, dextran sulfate, chondroitin sulfate and the like are possible. As other types of counter ion, mention is made of hydroxides, phosphates, glucuronates, citrates, carbonates, hydrogen carbonates, nitrates, cyanates, acetates, benzoates, bromides, chlorides and other inorganic or organic anions, and anionic polymers.

The pH of the internal aqueous phase may differ depending on the remote loading method. For instance, when using citric acid, it is necessary to preliminarily form a proton gradient (which may be called a proton concentration gradient or pH gradient) between the internal aqueous phase and the external aqueous phase. In this case, it is preferred that a difference in pH between the internal aqueous phase and the external aqueous phase is three or more. In the case of using ammonium sulfate, the proton gradient is established according to the chemical equilibrium, so that it is not needed to set a difference in pH between the internal aqueous phase and the external aqueous phase beforehand.

The liposome composition used for the long-lasting, controlled-release local anesthetic liposome preparation can be prepared by mixing, in a water-miscible solvent, a first aqueous phase solution with a water-miscible organic solution, in which a phospholipid and cholesterol are contained at a total concentration of 100 w/v % to 200 w/v %, at a ratio by volume of 3/1 to 12/1 in terms of the ratio to the unit volume of the water-miscible organic solution to obtain an emulsion wherein a total concentration of the phospholipid and cholesterol is at 15 w/v % to 50 w/v % in the resulting mixed phase, and subjecting the emulsion to external solution exchange with a second aqueous phase solution.

Liposome External Aqueous Phase (Second Aqueous Phase) Solution

For the external aqueous phase, there is used an aqueous solution whose ion concentration for forming the ion gradient is lower than the internal aqueous phase solution. More particularly, a HEPES solution, NaCl solution, or a sugar aqueous solution, such as of glucose or sucrose, is used. The pH of the external aqueous phase is preferably controlled with a buffering agent. In view of the decomposition of lipid and the difference in pH at the time of in vivo administration, the pH should be controlled preferably within a range of 5.5 to 8.5, more preferably within a range of 6.0 to 7.5. The osmotic pressure between the internal and external aqueous phases of the liposome may be so controlled as to be within a range not permitting the liposome to be destroyed due to a difference in osmotic pressure therebetween, and no specific limitation is placed thereon. Nevertheless, a smaller difference in the osmotic pressure is more preferred when taking the physical stability of the liposome into consideration.

Liposomes that May be Contained in the Liposome Composition

The liposome composition may further contain liposomes other than the above-defined liposome. The liposomes other than the above-defined liposome include a small-sized unilamellar liposome, a multivesicular liposome and the like. The content of the above-defined liposome is preferably not less than 50 wt % of a total liposome, more preferably not less than 60 wt %, much more preferably not less than 80 wt % and further more preferably not less than 90 wt %.

Liposome Preparation

The long-lasting, controlled-release local anesthetic liposome preparation can be prepared by encapsulating a local anesthetic in the liposome composition according to a remote loading method.

Remote Loading Method

The remote loading method is one wherein empty liposomes wherein no drug is encapsulated are prepared and a drug is added to the liposome external liquid thereby introducing the drug into the liposome. Using the remote loading method, the drug added to the external liquid is actively transferred to the liposome and taken therein. For this driving force, a solubility gradient, ion gradient, pH gradient or the like is used. For instance, an ion gradient can be formed across the liposome membrane so that the drug is introduced inside the liposome internal region. For a specific example, there is a technique wherein a drug is added to a liposome that has been preliminarily formed according to a remote loading method with respect to an Na+/K+ concentration gradient (see Japanese Patent Laid-Open No. Hei 9-20652).

The ion gradient method (ion concentration gradient method) is one wherein an ion gradient (ion concentration gradient) is formed between the internal-region aqueous phase and an external-region aqueous phase of the liposome, and a local anesthetic added to the external-region aqueous phase is transmitted through a liposome multilayer membrane according to the ion gradient to encapsulate the local anesthetic inside the liposome. For the ion gradient, a proton gradient (pH gradient) is preferred. With the ion gradient method, a liposome composition is prepared and a local anesthetic is added to the suspension of the liposome composition thereby enabling the introduction of the local anesthetic into the internal aqueous phase of the liposome.

For a method of forming a proton gradient (pH gradient), there can be used a method wherein a liposome is formed by use of an acidic pH buffer solution (e.g., a citric acid solution in the vicinity of a pH of 3) serving as a first aqueous phase, followed by adjusting the external pH of liposome to the vicinity of neutrality (e.g., the external aqueous phase is substituted with a buffer solution with a pH of 6.5) thereby forming a proton gradient (pH gradient) wherein the pH inside the liposome is lower than a pH outside the liposome.

Alternatively, the proton gradient may be formed through an ammonium ion gradient.

In this case, for example, an ammonium sulfate aqueous solution is used as a first aqueous phase to form liposomes and the ammonium sulfate is subsequently removed from the external aqueous phase of the liposome or is diluted to form a concentration gradient of the ammonium ion at least between the inside and outside of the liposome. At this time, ammonia migrates from the internal aqueous phase toward the external aqueous phase of the liposome by the formed concentration gradient. As a consequence, the protons derived from ammonia accumulate in the internal aqueous phase and thus, the inside of the liposome is more acidic than the outside thereby forming a proton gradient.

Local Anesthetic to be Encapsulated

The local anesthetics contained in the long-lasting, controlled-release local anesthetic liposome preparation are not specifically limited in type so far as they are ordinarily used as a local anesthetic. As preferred local anesthetics, mention is made of those which can be encapsulated inside the liposome according to an ion gradient method. The local anesthetic preferably has an ionizable and amphipathic nature, and should preferably be amphipathic and weakly basic.

Examples of the local anesthetic include: amino amide anesthetics, such as bupivacaine, ropivacaine, levobupivacaine, lidocaine, mepivacaine, prilocaine and salts thereof; and ester anesthetics, such as cocaine, procaine, tetracaine and salts thereof. Out of these, the amino amide anesthetics are preferred, among which bupivacaine, ropivacaine, levobupivacaine and salts thereof are more preferred. Besides, mention is made of opioid analgesic drugs such as morphine, fentanyl, codeine and the like.

The long-lasting, controlled-release local anesthetic liposome preparation can contain an effective amount of a local anesthetic. The amount of the local anesthetic contained in the long-lasting, controlled-release local anesthetic liposome preparation is not specifically limited and may be appropriately adjusted depending on the intended purpose. More particularly, where the long-lasting, controlled-release local anesthetic liposome preparation is administered to humans only once, the content can be determined as an amount sufficient to alleviate pain continuously at least for three days. For instance, when a long-lasting, controlled-release local anesthetic liposome preparation is administered once, an effective amount is persistently released at an operative wound area for not less than three days. As used herein, the term "administered once" means not only administration of a whole amount required for the local anesthetic at one site, but also administration of the required amount over several sites including an operative wound area and/or an adjacent site thereof, or the nerve periphery transmitting pain. The upper limit of the dosage is limited depending on the toxicity of individual local anesthetics. The lower limit of the dosage is not specifically limited because it is sufficient to release a local anesthetic in an internal region of liposome in a minimum dosage necessary for pain relief and such a required amount changes depending on the size of the operative wound. An accurate dosage varies depending on the characteristics of individual anesthetics and the factors of patients including age, gender, body weight, physical condition and the like.

The long-lasting, controlled-release local anesthetic liposome preparation has the capability of persistent, slow release for not less than three days or not less than four days. Thus, an effective amount is one permitting controlled-release for a duration of (not less than three days, or four to seven days). Accordingly, the amount of the local anesthetic contained at one administration of the long-lasting, controlled-release local anesthetic liposome preparation can be determined by multiplying an effective amount per kg with a human body weight and a controlled-release period of time of not less than three days or four to seven days.

Administration Method

Although the manner of administration of the long-lasting, controlled-release local anesthetic liposome preparation is not specifically limited, parenteral and local administration is preferred. For instance, selection can be made of subcutaneous, intramuscular, intraperitoneal, intrathecal, epidural, intraventricular, muscular tissue internervous connection and pain-transmitting nerve periphery routes. The manner of administration can be appropriately selected depending on the symptom, and administration can be made by at least one method selected from the group consisting of injection, infiltration, application and embedment. The manners of injection, infiltration, application and embedment are not specifically limited. These may include local manners. For instance, mention is made of: intramuscular injection and subcutaneous injection; subcutaneous infiltration; spray application; and sheet embedment. When a catheter is inserted into the body, for example, into the lumen or is inserted, for example, into the blood vessel and brought to a focal site, continuous or intermittent administration is possible via the catheter.

Where the long-lasting, controlled-release local anesthetic liposome preparation is administered through injection, administration is possible using an injector having an injection needle of 19 gauge to 34 gauge (G), for which the thickness of the injection needle can be appropriately chosen. Preferably, the gauge of the injection needle is conveniently selected depending on the site and manner of injection. For instance, with the case where intramuscular injection is slowly, reliably made, administration with a relatively thick injection needle is favorable, for which a 19 gauge to 25 gauge needle is preferred. With the infiltration administration, administration with a relatively fine needle is favorable, for which a 27 gauge to 34 gauge injection needle is preferred.

The site, to which the long-lasting, controlled-release local anesthetic liposome preparation is applied, includes, for example, an operative wound area and/or an adjacent site thereof, or a nerve periphery transmitting pain.

The types of operation at the operative wound site include, for example, gastrectomy, hepatectomy, appendectomy, Caesarean operation, cholecystectomy, hysterectomy, colectomy, prostatectomy, discectomy, oophorectomy, orthopedic operation, coronary artery bypass graft surgery, debridement and the like.

So far as the adjacent site of the operative wound area is one that is in contact with and/or near to the operative wound site, no limitation is placed thereon. So far as the nerve periphery transmitting the pain of the operative wound area is one that dominates the operative wound site, no specific limitation is placed thereon.

Further, the long-lasting, controlled-release local anesthetic liposome preparation can be administered to at least one site selected from the group consisting of subcutaneous, peritoneal, myofascial and intramuscular sites over the surgical would area and/or its adjacent site, or a nerve periphery transmitting pain.

The method for administering a long-lasting, controlled-release local anesthetic liposome preparation includes the steps of closing the fascia of an operative wound area having an incision site to be sutured, administering the long-lasting, controlled-release local anesthetic preparation along the operative wound to the fascia and/or the muscle therebeneath with an injection needle at a plurality of portions and totally closing the skin after the administration to the fascia and/or the muscle.

The method for administering a long-lasting, controlled-release local anesthetic liposome preparation may further include, after the closure with suturation, the step of uniformly, subcutaneously administering the long-lasting, controlled-release local anesthetic liposome preparation at a position in the vicinity of a suture thread along a sutured incision site and a position surrounding the incision site at a plurality of portions. The administration portion is not limited to one, and administration over a plurality of portions is preferred so that the long-lasting, controlled-release local anesthetic liposome preparation is uniformly administered along the operative wound. Preferably, the injection needle is stabbed vertically or inclinedly relative to the skin so as to permit its tip to come close to the sutured incision site.

The method for administering the long-lasting, controlled-release local anesthetic liposome preparation may further include the step of confirming, on the skin, a bloated feeling under the injected skin during the injection administration thereof. In this case, in order to confirm the subcutaneous bloated feeling on the skin, there can be used the hand of an operator or an instrument equipped with a pressure sensor. When the bloated feeling is confirmed, it can be also confirmed that the long-lasting, controlled-release local anesthetic liposome preparation is substantially administered and is uniformly diffused to the operative wound area.

The use of the long-lasting, controlled-release local anesthetic liposome preparation can bring about an analgesic effect for not less than three days after the administration and is able to bring about an analgesic period preferably of three to seven days and more preferably of three to five days.

Kit for Long-Lasting, Controlled Release Preparation

The kit for the long-lasting, controlled-release preparation includes the long-lasting, controlled-release local anesthetic liposome preparation and an injection needle whose gauge size is at least one of 27 gauge to 34 gauge. The injection needle may be single or plural in number, and the injection needle may be used singly or in combination of two or more with respect to its size. The liposome preparation may be administered by means of a fine needle such as a 27-gauge, 30-gauge or 34-gauge needle, thereby imposing a lower burden on patients. Since the liposome preparation being administered has high controlled-release properties, the utility of the kit for the long-lasting, controlled-release preparation is high.

Method for Applying Local Anesthetic

The method for applying a local anesthetic to mammals (except for humans) or humans by use of the long-lasting, controlled-release local anesthetic liposome preparation includes the step of administering the long-lasting, controlled-release local anesthetic liposome preparation to the mammal (except for a human) or human. Although the manner of administration is not specifically limited, it is preferred to use the above-described method of administering the long-lasting, controlled-release local anesthetic liposome preparation.

Next, illustrative embodiments will be described in more detail by way of examples, which should not be construed as limiting.

EXAMPLES

Preparation of Liposome Preparations (Lipids and Local Anesthetics)

In Examples 1 to 6 and Comparative Examples C1 and C2, liposome preparations were prepared using lipids and local anesthetics indicated below. In Preparatory Example P1, empty liposomes were prepared using lipids indicated below.

(1) Lipids

Hydrogenated soybean phosphatidylcholine (molecular weight: 790, SPC3 made by Lipoid GmbH) (abbreviated as "HSPC" in the examples)

Cholesterol (molecular weight: 388.66, made by Solvay S.A.) (abbreviated as "Chol" in the examples)

(2) Local Anesthetics

Bupivacaine hydrochloride (molecular weight: 324.89, made by JINAN CHENGHUI-SHUANGDA Chemical Co., Ltd.)

Ropivacaine hydrochloride (molecular weight: 310.88, made by JINAN CHENGHUI-SHUANGDA Chemical Co., Ltd.)

Preparatory Example P1

Empty liposomes were prepared according to a method set forth below.

(1) Preparation of Empty Liposomes

HSPC (2.82 g) and Chol (1.18 g) were each weighed, to which absolute ethanol (2 mL) was added so that a lipid concentration in the absolute ethanol was at 200 w/v %, followed by dissolution under heating at about 70° C. to prepare a lipid ethanol solution.

An internal aqueous phase solution (150 mM ammonium sulfate aqueous solution) (8 mL) serving as a first aqueous phase was added to the lipid ethanol solution (2 mL) prepared in this manner at such a ratio by volume of the internal aqueous phase to the lipid ethanol solution so that the internal aqueous phase/lipid ethanol solution=4/1 (v/v), followed by heating under agitation at a given speed of rotation for about ten minutes to prepare empty liposomes. The liposomes obtained after completion of the heating were quickly cooled with ice.

(2) Formation of pH Gradient

The empty liposomes after the ice cooling were subjected to external solution exchange by use of a centrifugal separator to form a pH gradient between the internal aqueous phase side/the external aqueous phase side of the liposomes.

The liposomes were dispersed in an about ten-fold amount of a 10 mM citric acid/NaCl solution (with a pH of 6.5), followed by centrifugal separation at 1,230×g for 15 minutes to precipitate the liposomes. Thereafter, the supernatant was removed. Subsequently, a 10 mM citric acid/NaCl solution having a pH of 6.5 was added for dispersion and subjected to centrifugal separation in a similar way. This was repeated three times.

Thereafter, a 10 mM phosphate buffer/NaCl solution (with a pH of 7.5) was added to so as to re-disperse the liposomes thereby forming a pH gradient. This was provided as the empty liposomes.

Example 1

A bupivacaine hydrochloride-containing, controlled-release preparation was prepared according to the method described below.

(1) Preparation of Empty Liposomes

HSPC (2.82 g) and Chol (1.18 g) were each weighed, to which absolute ethanol (2 mL) was added so that a lipid concentration in the absolute ethanol was at 200 w/v %, followed by dissolution under heating at about 70° C. to prepare a lipid ethanol solution.

An internal aqueous phase solution (150 mM ammonium sulfate aqueous solution) (8 mL) serving as a first aqueous phase was added to the lipid ethanol solution (2 mL) prepared in this manner at such a ratio by volume of the internal aqueous phase to the lipid ethanol solution so that the internal aqueous phase/lipid ethanol solution=4/1 (v/v), followed by heating under agitation at a given speed of rotation for about ten minutes to prepare empty liposomes. The liposomes obtained after completion of the heating were quickly cooled with ice.

(2) Formation of pH Gradient

The empty liposomes after the ice cooling were subjected to external solution exchange by use of a centrifugal separator to form a pH gradient between the internal aqueous phase side/the external aqueous phase side of the liposomes.

The liposomes were dispersed in an about ten-fold amount of a 10 mM citric acid/NaCl solution (with a pH of 6.5), followed by centrifugal separation at 1,230×g for 15 minutes to precipitate the liposomes. Thereafter, the supernatant was removed. Subsequently, a 10 mM citric acid/NaCl solution (with a pH of 6.5) was added for dispersion and subjected to centrifugal separation in a similar way. This was repeated three times.

Thereafter, a 10 mM citric acid/NaCl solution (with a pH of 6.5) was added so as to re-disperse the empty liposomes thereby forming a pH gradient.

(3) Introduction of a Local Anesthetic by Use of the pH Gradient

The amounts of HSPC and cholesterol in the empty liposomes after the formation of pH gradient were quantitatively determined to obtain a total lipid concentration. Based on the total lipid concentration obtained in this manner, an amount of bupivacaine hydrochloride used as a local anesthetic was so calculated that a ratio of local anesthetic/total lipid (mol/mol) was set at 0.4. A required amount of the local anesthetic was weighed, followed by adding reverse osmosis (RO) water to prepare 10 mg/mL of the local anesthetic solution.

A given amount of the local anesthetic solution heated to 65° C. beforehand was added to the liposome dispersion liquid heated to 65° C., followed by heating under agitation at 65° C. for 60 minutes to introduce the drug. The liposomes after the introduction of the local anesthetic were quickly cooled with ice.

(4) Removal of Unencapsulated Local Anesthetic

A 10 mM citric acid/NaCl solution (with a pH of 6.5) was added so as to disperse the liposomes after the introduction of the local anesthetic, followed by centrifugal separation at 1,230×g for 15 minutes to precipitate the liposomes. Thereafter, the supernatant was removed. Subsequently, a 10 mM citric acid/NaCl solution (with a pH of 6.5) was added so as to disperse the liposomes and subjected to centrifugal separation in a similar way. This was repeated three times to remove the unencapsulated local anesthetic. After removal of the supernatant after the third cycle, a 20 mM HEPES/NaCl solution (with a pH of 7.5) was added so as to re-disperse the liposomes to prepare a long-lasting, controlled-release local anesthetic preparation. This preparation was provided as a bupivacaine hydrochloride-containing, controlled-release preparation.

Example 2

A ropivacaine hydrochloride-containing, controlled-release preparation was prepared according to the method described below.
(1) Preparation of Empty Liposomes HSPC (141.2 g) and Chol (58.82 g) were each weighed, to which absolute ethanol (200 mL) was added so that a lipid concentration in the absolute ethanol was at 100 w/v %, followed by dissolution under heating at about 70° C. to prepare a lipid ethanol solution.

An internal aqueous phase solution (150 mM ammonium sulfate aqueous solution) (650 mL) serving as a first aqueous phase was added to the lipid ethanol solution (200 mL) prepared in this manner at such a ratio by volume of the internal aqueous phase to the lipid ethanol solution so that the internal aqueous phase/lipid ethanol solution=3.3/1 (v/v), followed by heating under agitation at a given speed of rotation for about 60 minutes to prepare empty liposomes. The liposomes obtained after completion of the heating were quickly cooled with ice.
(2) Formation of pH Gradient The empty liposomes after the ice cooling were subjected to external solution exchange by use of a centrifugal separator to form a pH gradient between the internal aqueous phase side/the external aqueous phase side of the liposomes.

The liposomes were dispersed in an about three-fold amount of a 10 mM citric acid/NaCl solution (with a pH of 6.5), followed by centrifugal separation at 4,200×g for 20 minutes to precipitate the liposomes. Thereafter, the supernatant was removed. Subsequently, a 10 mM citric acid/NaCl solution (with a pH of 6.5) was added for dispersion and subjected to centrifugal separation in a similar way. This was repeated three times.

Thereafter, a 10 mM citric acid/NaCl solution (with a pH of 6.5) was added so as to re-disperse the empty liposomes thereby forming a pH gradient.
(3) Introduction of a Local Anesthetic by Use of the pH Gradient The amounts of HSPC and cholesterol in the empty liposomes after the formation of pH gradient were quantitatively determined to obtain a total lipid concentration. Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution to the liposome dispersion liquid, the drug was introduced by heating under agitation at 60° C. for 120 minutes. The liposomes after the introduction of the local anesthetic were quickly cooled with ice.
(4) Removal of Unencapsulated Local Anesthetic A 10 mM citric acid/NaCl solution (with a pH of 6.5) was added so as to disperse the liposomes after the introduction of the local anesthetic, followed by centrifugal separation at 4,200×g for 20 minutes to precipitate the liposomes. Thereafter, the supernatant was removed. Subsequently, a 10 mM phosphate buffer/NaCl solution (with a pH of 7.5) was added so as to disperse the liposomes and subjected to centrifugal separation in a similar way. This was repeated three times so as to remove the unencapsulated local anesthetic. After third removal of the supernatant, a 10 mM phosphate buffer/NaCl solution (with a pH of 7.5) was added so as to re-disperse the liposomes to prepare a long-lasting, controlled-release local anesthetic preparation. This preparation was provided as a ropivacaine hydrochloride-containing, controlled-release preparation.

Example 3

A ropivacaine hydrochloride-containing, controlled-release preparation was prepared according to the method described below.
(1) Preparation of Empty Liposomes HSPC (169.4 g) and Chol (70.62 g) were each weighed, to which absolute ethanol (180 mL) was added so that a lipid concentration in the absolute ethanol was at 133 w/v %, followed by dissolution under heating at about 70° C. to prepare a lipid ethanol solution.

An internal aqueous phase solution (150 mM ammonium sulfate aqueous solution) (600 mL) serving as a first aqueous phase was added to the lipid ethanol solution (180 mL) prepared in this manner at such a ratio by volume of the internal aqueous phase to the lipid ethanol solution so that the internal aqueous phase/lipid ethanol solution=3.3/1 (v/v), followed by heating under agitation by means of a TK homomixer MARK II at a given speed of rotation for about 60 minutes to prepare empty liposomes. The liposomes obtained after completion of the heating were quickly cooled with ice.
(2) Formation of pH Gradient The empty liposomes after the ice cooling were subjected to external solution exchange by use of a centrifugal separator to form a pH gradient between the internal aqueous phase side/the external aqueous phase side of the liposomes.

The liposomes were dispersed in an about three-fold amount of a 20 mM citric acid/NaCl solution (with a pH of 6.5), followed by centrifugal separation at 4,200×g for 20 minutes to precipitate the liposomes. Thereafter, the supernatant was removed. Subsequently, a 20 mM citric acid/NaCl solution (with a pH of 6.5) was added for dispersion and subjected to centrifugal separation in a similar way. This was repeated three times.

Thereafter, a 20 mM citric acid/NaCl solution (with a pH of 6.5) was added so as to re-disperse the empty liposomes thereby forming a pH gradient.
(3) Introduction of a Local Anesthetic by Use of the pH Gradient The amounts of HSPC and cholesterol in the empty liposomes after the formation of pH gradient were quantitatively determined to obtain a total lipid concentration. Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution to the liposome dispersion liquid, the drug was introduced by heating under agitation at 60° C. for 120 minutes. The liposomes after the introduction of the local anesthetic were quickly cooled with ice.
(4) Removal of Unencapsulated Local Anesthetic A 20 mM citric acid/NaCl solution (with a pH of 6.5) was added so as to disperse the liposomes after the introduction of the local anesthetic, followed by centrifugal separation at 4,200×g for 20 minutes to precipitate the liposomes. Thereafter, the supernatant was removed. Subsequently, a 20 mM phosphate buffer/NaCl solution (with a pH of 7.2) was added so as to disperse the liposomes and subjected to centrifugal separation in a similar way. This was repeated three times to remove the unencapsulated local anesthetic. After the third removal of the supernatant, a 20 mM phosphate buffer/NaCl solution (with a pH of 7.2) was added so as to re-disperse the liposomes thereby preparing a long-lasting, controlled-release local anesthetic preparation. This preparation was provided as a ropivacaine hydrochloride-containing, controlled-release preparation.

Example 4

A ropivacaine hydrochloride-containing, controlled-release preparation was prepared according to the method described below.
(1) Preparation of Empty Liposomes HSPC (211.7 g) and Chol (88.3 g) were each weighed, to which absolute ethanol (200 mL) was added so that a lipid concentration in the absolute ethanol was at 150 w/v %, followed by dissolution under heating at about 70° C. to prepare a lipid ethanol solution.

An internal aqueous phase solution (150 mM ammonium sulfate aqueous solution) (800 mL) serving as a first aqueous phase was added to the lipid ethanol solution (200 mL) prepared in this manner at such a ratio by volume of the internal aqueous phase to the lipid ethanol solution so that the internal aqueous phase/lipid ethanol solution=4/1 (v/v), followed by heating under agitation at a given speed of rotation for about 60 minutes to prepare empty liposomes. The liposomes obtained after completion of the heating were quickly cooled with ice.
(2) Formation of pH Gradient The empty liposomes after the ice cooling were subjected to external solution exchange by use of a centrifugal separator to form a pH gradient between the internal aqueous phase side/the external aqueous phase side of the liposomes.

The liposomes were dispersed in an about three-fold amount of a 20 mM citric acid/NaCl solution (with a pH of 6.5), followed by centrifugal separation at 4,200×g for 20 minutes to precipitate the liposomes. Thereafter, the supernatant was removed. Subsequently, a 20 mM citric acid/NaCl solution (with a pH of 6.5) was added for dispersion and subjected to centrifugal separation in a similar way. This was repeated three times.

Thereafter, a 20 mM citric acid/NaCl solution (with a pH of 6.5) was added so as to re-disperse the empty liposomes thereby forming a pH gradient.
(3) Introduction of a Local Anesthetic by Use of the pH Gradient The amounts of HSPC and cholesterol in the empty liposomes after the formation of pH gradient were quantitatively determined to obtain a total lipid concentration. Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution to the liposome dispersion liquid, the drug was introduced by heating under agitation at 60° C. for 120 minutes. The liposomes after the introduction of the local anesthetic were quickly cooled with ice.

(4) Removal of Unencapsulated Local Anesthetic

A 20 mM citric acid/NaCl solution (with a pH of 6.5) was added so as to disperse the liposomes after the introduction of the local anesthetic, followed by centrifugal separation at 4,200×g for 20 minutes to precipitate the liposomes. Thereafter, the supernatant was removed. Subsequently, a 20 mM phosphate buffer/NaCl solution (with a pH of 7.2) was added so as to disperse the liposomes and subjected to centrifugal separation in a similar way. This was repeated three times to remove the unencapsulated local anesthetic. After the third removal of the supernatant, a 10 mM phosphate buffer/NaCl solution (with a pH of 7.2) was added so as to re-disperse the liposomes thereby preparing a long-lasting, controlled-release local anesthetic preparation. This preparation was provided as a ropivacaine hydrochloride-containing, controlled-release preparation.

Example 5

A ropivacaine hydrochloride-containing, controlled-release preparation was prepared according to the method described below.
(1) Preparation of Empty Liposomes HSPC (141.2 g) and Chol (58.82 g) were each weighed, to which absolute ethanol (200 mL) was added so that a lipid concentration in the absolute ethanol was at 100 w/v %, followed by dissolution under heating at about 70° C. to prepare a lipid ethanol solution.

An internal aqueous phase solution (150 mM ammonium sulfate aqueous solution) (650 mL) serving as a first aqueous phase was added to the lipid ethanol solution (200 mL) prepared in this manner at such a ratio by volume of the internal aqueous phase to the lipid ethanol solution so that the internal aqueous phase/lipid ethanol solution=3.3/1 (v/v), followed by heating under agitation at a given speed of rotation for about 60 minutes to prepare empty liposomes. The liposomes obtained after completion of the heating were quickly cooled with ice.
(2) Formation of pH Gradient The empty liposomes after the ice cooling were subjected to external solution exchange by use of a centrifugal separator to form a pH gradient between the internal aqueous phase side/the external aqueous phase side of the liposomes.

The liposomes were dispersed in an about three-fold amount of a 20 mM citric acid/NaCl solution (with a pH of 6.5), followed by centrifugal separation at 4,200×g for 20 minutes to precipitate the liposomes. Thereafter, the supernatant was removed. Subsequently, a 20 mM citric acid/NaCl solution (with a pH of 6.5) was added for dispersion and subjected to centrifugal separation in a similar way. This was repeated three times.

Thereafter, a 20 mM citric acid/NaCl solution (with a pH of 6.5) was added so as to re-disperse the empty liposomes thereby forming a pH gradient.
(3) Introduction of a Local Anesthetic by Use of the pH Gradient The amounts of HSPC and cholesterol in the empty liposomes after the formation of pH gradient were quantitatively determined to obtain a total lipid concentration. Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution to the liposome dispersion liquid, the drug was introduced by heating under agitation at 60° C. for 120 minutes. The liposomes after the introduction of the local anesthetic were quickly cooled with ice.

(4) Removal of Unencapsulated Local Anesthetic

A 20 mM citric acid/NaCl solution (with a pH of 6.5) was added so as to disperse the liposomes after the introduction of the local anesthetic, followed by centrifugal separation at 4,200×g for 20 minutes to precipitate the liposomes. Thereafter, the supernatant was removed. Subsequently, a 20 mM phosphate buffer/NaCl solution (with a pH of 7.2) was added so as to disperse the liposomes and subjected to centrifugal separation in a similar way. This was repeated three times to remove the unencapsulated local anesthetic. After the removal of the supernatant formed after the third repetition, a 20 mM phosphate buffer/NaCl solution (with a pH of 7.2) was added so as to re-disperse the liposomes thereby preparing a long-lasting, controlled-release local anesthetic preparation. This preparation was provided as a ropivacaine hydrochloride-containing, controlled-release preparation.

Example 6

A ropivacaine hydrochloride-containing, controlled-release preparation was prepared according to the method described below.

(1) Preparation of Empty Liposomes

HSPC (70.6 g) and Chol (29.4 g) were each weighed, to which absolute ethanol (65 mL) was added so that a lipid concentration in the absolute ethanol was at 150 w/v %, followed by dissolution under heating at about 70° C. to prepare a lipid ethanol solution.

An internal aqueous phase solution (150 mM ammonium sulfate aqueous solution) (250 mL) serving as a first aqueous phase was added to the lipid ethanol solution (65 mL) prepared in this manner at such a ratio by volume of the internal aqueous phase to the lipid ethanol solution so that the internal aqueous phase/lipid ethanol solution=4/1 (v/v), followed by heating under agitation at a given speed of rotation for about 60 minutes by CLEARMIX single motion to prepare empty liposomes. The liposomes obtained after completion of the heating were quickly cooled with ice.

(2) Formation of pH Gradient

The empty liposomes after the ice cooling were subjected to external solution exchange by use of a centrifugal separator to form a pH gradient between the internal aqueous phase side/the external aqueous phase side of the liposomes.

The liposomes were dispersed in an about three-fold amount of a 20 mM citric acid/NaCl solution (with a pH of 6.5), followed by centrifugal separation at 100,000×g for 20 minutes to precipitate the liposomes. Thereafter, the supernatant was removed. Subsequently, a 20 mM citric acid/NaCl solution (with a pH of 6.5) was added for dispersion and subjected to centrifugal separation in a similar way. This was repeated three times.

Thereafter, a 20 mM citric acid/NaCl solution (with a pH of 6.5) was added to so as to re-disperse the empty liposomes thereby forming a pH gradient.

(3) Introduction of a Local Anesthetic by Use of the pH Gradient

The amounts of HSPC and cholesterol in the empty liposomes after the formation of pH gradient were quantitatively determined to obtain a total lipid concentration. Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution to the liposome dispersion liquid, the drug was introduced by heating under agitation at 60° C. for 120 minutes. The liposomes after the introduction of the local anesthetic were quickly cooled with ice.

(4) Removal of Unencapsulated Local Anesthetic

A 20 mM citric acid/NaCl solution (with a pH of 6.5) was added so as to disperse the liposomes after the introduction of the local anesthetic, followed by centrifugal separation at 100,000×g for 20 minutes to precipitate the liposomes. Thereafter, the supernatant was removed. Subsequently, a 20 mM phosphate buffer/NaCl solution (with a pH of 7.2) was added so as to disperse the liposomes and subjected to centrifugal separation in a similar way. This was repeated three times to remove the unencapsulated local anesthetic. After the third removal of the supernatant, a 20 mM phosphate buffer/NaCl solution (with a pH of 7.2) was added so as to re-disperse the liposomes thereby preparing a long-lasting, controlled-release local anesthetic preparation. This preparation was provided as a ropivacaine hydrochloride-containing, controlled-release preparation.

Example 7

A ropivacaine hydrochloride-containing, controlled-release preparation was prepared according to the method described below.

(1) Preparation of Empty Liposomes

HSPC (112.90 g) and Chol (47.10 g) were each weighed, to which absolute ethanol (120 mL) was added so that a lipid concentration in the absolute ethanol was at 133 w/v %, followed by dissolution under heating at about 70° C. to prepare a lipid ethanol solution.

An internal aqueous phase solution (300 mM citric acid aqueous solution with a pH of 3.0) (400 mL) serving as a first aqueous phase was added to the lipid ethanol solution (120 mL) prepared in this manner at such a ratio by volume of the internal aqueous phase to the lipid ethanol solution so that the internal aqueous phase/lipid ethanol solution=3.3/1 (v/v), followed by agitation for about three minutes by means of a stirrer. After the agitation, empty liposomes were prepared by further agitation under heating by means of a homomixer for about 45 minutes at a given speed of rotation. The liposomes obtained after completion of the heating were quickly cooled with ice.

(2) Formation of pH Gradient

The empty liposomes after the ice cooling were subjected to external solution exchange by use of a centrifugal separator to form a pH gradient between the internal aqueous phase side/the external aqueous phase side of the liposomes.

The liposomes were dispersed in an about three-fold amount of a 20 mM citric acid/NaCl solution (with a pH of 6.5), followed by centrifugal separation at 100,000×g for 20 minutes to precipitate the liposomes. Thereafter, the supernatant was removed. Subsequently, a 20 mM citric acid/NaCl solution (with a pH of 6.5) was added for dispersion and subjected to centrifugal separation in a similar way. This was repeated three times.

(3) Introduction of a Local Anesthetic by Use of the pH Gradient

The amounts of HSPC and cholesterol in the empty liposomes after the formation of pH gradient were quantitatively determined to obtain a total lipid concentration. Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution to the liposome dispersion liquid, the drug was introduced by heating under agitation at 60° C. for 60 minutes. The liposomes after the introduction of the local anesthetic were quickly cooled with ice.

(4) Removal of Unencapsulated Local Anesthetic

A 20 mM citric acid/NaCl solution (with a pH of 6.5) was added so as to disperse the liposomes after the introduction of the local anesthetic, followed by centrifugal separation at 100,000×g for 20 minutes to precipitate the liposomes. Thereafter, the supernatant was removed. Subsequently, a 20 mM phosphate buffer/NaCl solution (with a pH of 7.2) was added so as to disperse the liposomes and subjected to centrifugal separation in a similar way. This was repeated four times to remove the unencapsulated local anesthetic, thereby preparing a long-lasting, controlled-release local anesthetic preparation. This preparation was provided as a ropivacaine hydrochloride-containing, controlled-release preparation.

Comparative Example C1

A ropivacaine hydrochloride-containing preparation was prepared according to an existing method. This is specifically described below.

(1) Preparation of Empty Liposomes

HSPC (1.41 g) and Chol (0.59 g) were so weighed that HSPC/Chol=54/46 (molar ratio), to which chloroform (25 mL) was added so as to dissolve the lipids therein thereby obtaining a lipid chloroform solution.

Using a rotary evaporator, the solvent was removed from the lipid chloroform solution to form a thin film. Next, according to a known method, the film was hydrated by adding an internal aqueous phase solution (150 mM ammonium sulfate aqueous solution) thereto so as to make a lipid concentration of about 4%. Agitation under heating to 65° C. was carried out to form liposomes, followed by quick cooling with ice.

(2) Formation of pH Gradient

The resulting empty liposomes after the ice cooling were subjected to external solution exchange by use of a centrifugal separator to form a pH gradient between the internal aqueous phase side/the external aqueous phase side in the liposomes. The liposomes were dispersed in an about two-fold amount of a 10 mM citric acid/NaCl solution (with a pH of 6.5), followed by centrifugal separation at 1,230×g for 20 minutes to precipitate the empty liposomes. Thereafter, the supernatant was removed. Subsequently, a 10 mM citric acid/NaCl solution (with a pH of 6.5) was added for dispersion and subjected to centrifugal separation in a similar way. This was repeated three times.

Thereafter, a 10 mM citric acid/NaCl solution (with a pH of 6.5) was added so as to re-disperse the liposomes thereby forming a pH gradient.

(3) Introduction of a Local Anesthetic by Use of the pH Gradient

The amounts of HSPC and cholesterol in the empty liposomes after the formation of pH gradient were quantitatively determined to obtain a total lipid concentration. Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution to the liposome dispersion liquid, the drug was introduced by heating at 60° C. for 120 minutes. The liposomes after the introduction of the local anesthetic were quickly cooled with ice.

(4) Removal of Unencapsulated Local Anesthetic

A 10 mM citric acid/NaCl solution (with a pH of 6.5) was added so as to disperse the liposomes after the introduction of the local anesthetic, followed by centrifugal separation at 1,230×g for 20 minutes to precipitate the liposomes. Thereafter, the supernatant was removed. Subsequently, a 10 mM phosphate buffer/NaCl solution (with a pH of 7.2) was added so as to disperse the liposomes and subjected to centrifugal separation in a similar way. This was repeated three times to remove the unencapsulated local anesthetic, thereby preparing a long-lasting, controlled-release local anesthetic preparation. The long-lasting local anesthetic preparation obtained in this manner was provided as a ropivacaine hydrochloride-containing preparation.

Comparative Example C2

A ropivacaine hydrochloride-containing preparation was prepared according to an existing method (extrusion method). This is specifically described below.

(1) Preparation of Empty Liposomes

HSPC (0.71 g) and cholesterol (0.29 g) were so weighed that HSPC/Chol=54/46 (molar ratio), to which absolute ethanol (1 mL) was added so as to dissolve the lipids under heating thereby obtaining a lipid ethanol solution.

A 150 mM ammonium sulfate aqueous solution (internal aqueous phase) (9 mL), heated to about 70° C., was added to the lipid ethanol solution (1 mL) obtained in this manner, followed by agitation under heating by use of a ultrasonic apparatus to prepare a crude liposome suspension.

The crude liposome suspension obtained in this manner was sequentially passed through filters (pore size 1.0 μm×five times, made by Whatman PLC) attached to an extruder (The Extruder T. 10, made by Lipex Biomembranes, Inc.) heated to about 70° C. to form empty liposomes, followed by quick cooling with ice.

(2) Formation of pH Gradient

The empty liposomes after the ice cooling were subjected to external solution exchange by use of a centrifugal separator to form a pH gradient between the internal aqueous phase side/the external aqueous phase side in the liposomes.

The liposomes were dispersed in an about two-fold amount of a 10 mM citric acid/NaCl solution (with a pH of 6.5), followed by treatment at 100,000×g for 10 minutes to precipitate the empty liposomes. Thereafter, the supernatant was removed. Subsequently, a 10 mM citric acid/NaCl solution (with a pH of 6.5) was added to disperse the liposomes and subjected to centrifugal separation in a similar way. This was repeated three times.

Thereafter, a 10 mM citric acid/NaCl solution (with a pH of 6.5) was added so as to re-disperse the empty liposomes thereby forming a pH gradient.

(3) Introduction of a Local Anesthetic by Use of the pH Gradient

The amounts of HSPC and cholesterol in the empty liposomes after the formation of pH gradient were quantitatively determined to obtain a total lipid concentration.

Based on the total lipid concentration obtained in this manner, an amount of ropivacaine hydrochloride used as a local anesthetic was so calculated that a ratio of local anesthetic/total lipid (mol/mol) was set at 0.4. A required amount of the local anesthetic was weighed, followed by adding RO water thereby preparing 40 mg/mL of a local anesthetic solution.

After addition of a given amount of the local anesthetic solution, heated to 65° C. beforehand, to the liposome dispersion liquid heated to 65° C., the drug was introduced by heating under agitation at 65° C. for 60 minutes. The liposomes after the introduction of the local anesthetic were quickly cooled with ice.

(4) Removal of Unencapsulated Local Anesthetic

A 10 mM citric acid/NaCl solution (with a pH of 6.5) was added so as to disperse the liposomes after the introduction of the local anesthetic, followed by treatment with a centrifugal separator at 100,000×g for ten minutes to precipitate the liposomes. Thereafter, the supernatant was removed, to which a 10 mM citric acid/NaCl solution (with a pH of 6.5) was added to for dispersion, followed by treatment with a centrifugal separator in a similar way. This was repeated three times to remove the unencapsulated local anesthetic. After the third removal of the supernatant, a 20 mM phosphate buffer/NaCl solution (with a pH of 7.2) was added so as to re-disperse the liposomes thereby preparing a local anesthetic preparation. The resulting local anesthetic preparation was provided as a ropivacaine hydrochloride-containing preparation.

Comparative Example C3

Exparel (registered trademark) (made by Pacira Pharmaceuticals, Inc.), which is a commercially available bupivacaine-containing liposome preparation, was prepared.

Evaluation of Characteristics of the Prepared Liposome Preparations

The amount of local anesthetic in and average particle diameter of individual liposome preparations of Examples 1 to 7, Preparatory Example P1, and Comparative Examples C1 and C2 were measured with the results shown in Table 1.

Amount of Local Anesthetic

Based on a local anesthetic concentration (molar concentration) and a total lipid concentration (molar concentration) encapsulated in liposomes, the amount of the local anesthetic encapsulated in the liposomes was determined as local anesthetics/total lipids (molar ratio).

Average Particle Diameter

The average particle diameter (d50; μm) was measured by use of a light scattering diffraction size distributor (LS230, made by Beckman Coulter, Inc.).

Lamellarity of Liposome Membrane

A transmission electron microscopic (TEM) photograph of a sample piece prepared by use of a microtome was taken and the number of layer structures was counted to measure the lamellarity of the liposome membrane.

TABLE 1

| Examples/Preparatory Example | Amount of carried local anesthetic (local anesthetic/total lipid)[mol/mol] | Average particle diameter of liposomes [μm] | Lamellarity of liposome membrane [layers] |
| --- | --- | --- | --- |
| Examples/Comparative examples | Amount of mounted local anesthetics (Local anesthetics/Total lipids)[mol/mol] | Average diameter of liposomes [μm] | Lamellarity of liposomal walls [layers] |
| 1 | 0.10 | 9.5 | ≥12 |
| 2 | 0.15 | 9.4 | ≥12 |
| 3 | 0.14 | 3.4 | c.a. 12 |
| 4 | 0.18 | 7.7 | ≥12 |
| 5 | 0.17 | 12 | ≥12 |
| 6 | 0.11 | 1.5 | c.a. 10 |
| 7 | 0.22 | 4.9 | ≥12 |
| P1 | — | 2.5 | ≥12 |
| C1 | 0.15 | 13 | MLV |
| C2 | 0.19 | 0.9 | LUV |

When comparing the bupivacaine hydrochloride-containing, controlled-release preparation of Example 1 and the ropivacaine hydrochloride-containing, controlled-release preparations of Examples 2 to 7 with the ropivacaine hydrochloride-containing preparation of Comparative Example C1 prepared according to the existing method, the preparation of Comparative Example C1 has a difficulty in controlling the particle diameter. Moreover, the drug concentration in the external liquid even after removal of the unencapsulated drug was higher by about nine times compared to the bupivacaine hydrochloride-containing, controlled-release preparation of Example 1 and the ropivacaine hydrochloride-containing, controlled-release preparation of Example 2. From this, it was revealed that the ropivacaine hydrochloride-containing preparation prepared in Comparative Example C1 did not stably retain the local anesthetic inside the liposomes. This is considered due to the fact that the structure of the liposome of Comparative Example C1 differs from the structure of the liposomes of Examples 1 to 7.

Comparison in Stability of Liposome Preparations

The stabilities (drug leakages) of the ropivacaine hydrochloride-containing, controlled-release preparations of Example 2 to 5 and the ropivacaine hydrochloride-containing preparation of Comparative Example C1 were compared by subjecting the preparations to a heating test at 37° C.

(1) Method

The ropivacaine hydrochloride-containing, controlled-release preparations of Example 2 to 5 and the ropivacaine hydrochloride-containing preparation of Comparative Example C1 were diluted with a phosphate buffer so that the concentration of the ropivacaine hydrochloride was set at 0.6 mg/mL (dosage). The preparations after the dilution were provided as a sample and heated at 37° C. for given times (zero hours (unheated), 0.25 hours, 0.5 hours, one hour, two hours, four hours, six hours, 18 hours, 24 hours, 48 hours and 72 hours).

After the heating, the samples were immediately removed and quickly cooled with ice, thereby stopping the release of the local anesthetic from the liposome composition.

The amount of released ropivacaine hydrochloride (release amount) was quantitatively determined as follows: a liposome preparation was diluted with RO water (water purified by means of a reverse osmosis membrane) to have a total lipid concentration of about 20 mg/mL to 30 mg/mL in the liposome preparation, followed by 20-fold dilution with methanol to destroy the liposomes; and quantitative determination was made according to high-performance liquid chromatography using a ultraviolet-visible spectrophotometer at an absorbance of 263 nm of this solution.

(2) Results

The release rate (%) of ropivacaine hydrochloride of the respective samples was calculated from the input and release and shown in FIG. 1. It will be noted that in FIG. 1, "Ex." means example and "Comp. ex." means comparative example. In FIG. 1, "Time [hr.]" of the abscissa means "elapse time (hours) from commencement of heating," and "Release rates of ropivacaine hydrochloride [mass %]" of the ordinate means "release rates of ropivacaine hydrochloride (mass %)."

It was revealed that the ropivacaine hydrochloride-containing, controlled-release preparations of the illustrative embodiments (Examples 2 to 5) were low in initial leakage rate of the drug and allowed gentle release with time. On the other hand, the ropivacaine hydrochloride-containing preparation prepared by the existing method (Comparative Example C1) was very high in initial leakage rate of the drug and subsequently allowed gentle release with time. In other words, it is considered that the ropivacaine hydrochloride preparation prepared by the existing method has a very high amount of the local anesthetic contained in the external liquid of the preparation obtained immediately after the preparation (an amount of the local anesthetic unencapsulated in the liposome composition), thus leading to the immediate initial release. Accordingly, it has been demonstrated that the ropivacaine hydrochloride preparation prepared by the existing method could not stably encapsulate the local anesthetic in the liposome composition. This is considered to present not only concern on the storage stability of the preparation, but also a risk of an adverse effect because of the danger of causing an initial burst after administration. Accordingly, it has been suggested that the local anesthetic prepared according to the existing method involves a difficulty in providing safety on a clinical basis.

Comparison of Drug Kinetics of Liposome Preparations

The ropivacaine hydrochloride-containing, controlled-release preparation of Example 2 and the ropivacaine-containing preparation of Comparative Example C1 were subjected to a drug-kinetic test, with the results being compared with each other.

(1) Method

Ten-week-old-male Wistar rats were anesthetized through 2% enflurane inhalation. Thereafter, the ropivacaine hydrochloride-containing, controlled-release preparation of Example 2 (0.87 mg/body in terms of an amount of ropivacaine hydrochloride) or the ropivacaine-containing preparation of Comparative Example C1 (0.95 mg/body in term of an amount of ropivacaine hydrochloride) was administered to the plantaris muscle of the rats.

As to the rats administered with the ropivacaine hydrochloride-containing, controlled-release preparation of Example 2, the plantaris muscle tissue at the administered site was harvested at elapse times of four hours, 24 hours, 48 hours, 72 hours, 120 hours, 168 hours and 216 hours after the administration. On the other hand, with respect to the rat administered with the ropivacaine hydrochloride-containing preparation of Comparative Example C1, the plantaris muscle tissue at the administered site was harvested at elapse times of four hours, 24 hours, 72 hours and 120 hours after the administration.

The harvested plantaris muscle tissues were subjected to homogenate treatment to prepare a homogenate solution.

Subsequently, the homogenate solution was processed and the resulting sample solution was subjected to quantitative determination with high-performance liquid chromatography (detection wavelength: 210 nm) to obtain an amount of the ropivacaine hydrochloride left in the plantaris muscle tissue (sample) at the administration site.

(2) Results

Figure 2:
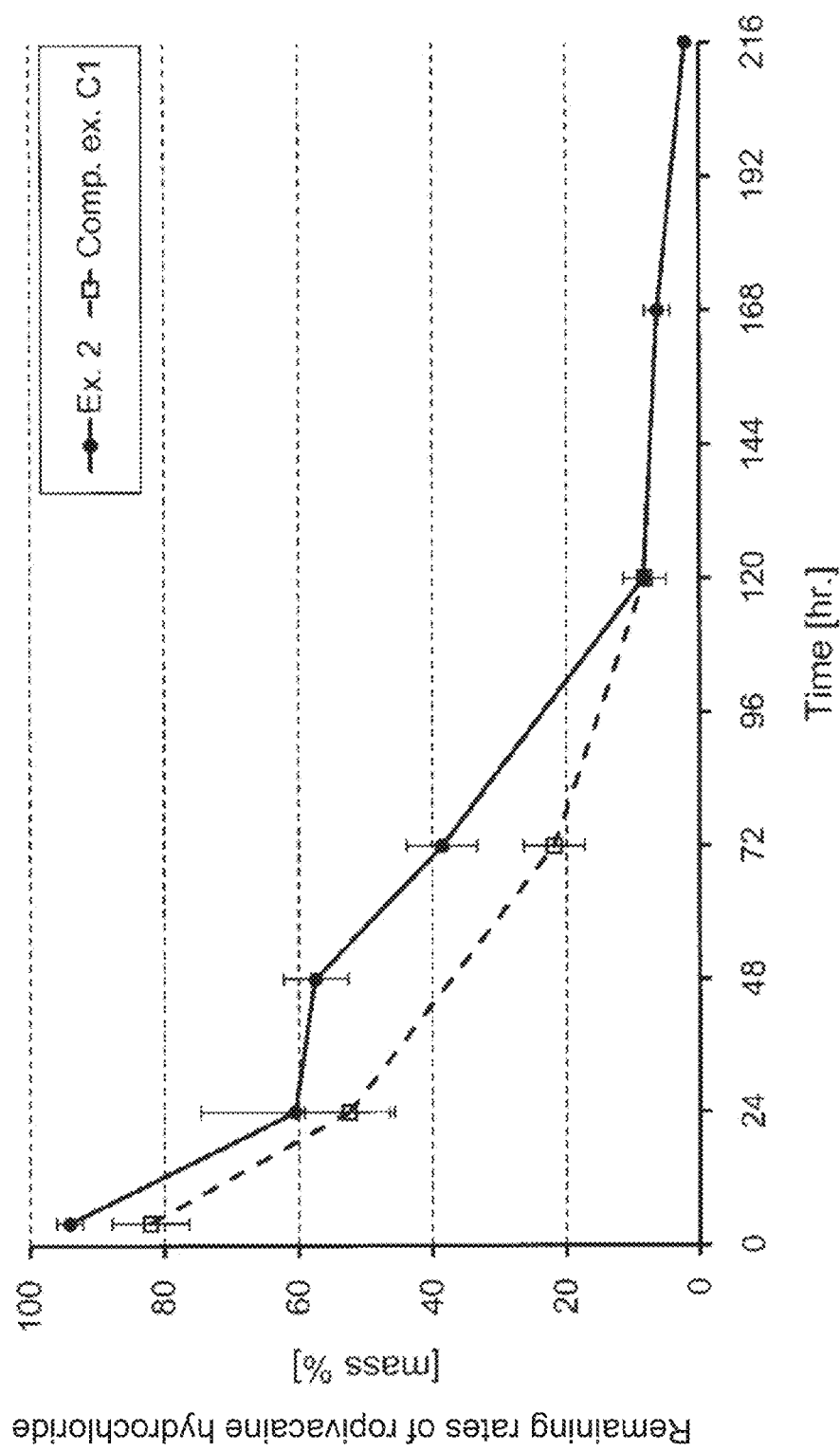
FIG. 2 is a graph showing a timewise change in remaining rate (%) of ropivacaine hydrochloride at an administration site of a ropivacaine hydrochloride-containing, controlled-release preparation of Example 2 and a ropivacaine hydrochloride-containing preparation of Comparative Example C1 prepared according to an existing method.

The remaining rates (%) of the ropivacaine hydrochloride in the respective samples were calculated from the amount (dosage) of the ropivacaine hydrochloride dosed to the rat and the amount (residual amount) of ropivacaine hydrochloride left in the sample, and are shown in FIG. 2. It will be noted that in FIG. 2, "Ex." means the example and "Comp. ex." means the comparative example. In FIG. 2, "Time [hr.]" of the abscissa means "elapse time (hours) after administration," and "Remaining rates of ropivacaine hydrochloride [mass %]" of the ordinate means "residual rates of ropivacaine hydrochloride (mass %)."

As to the ropivacaine hydrochloride-containing, controlled-release preparation of Example 2, the ropivacaine hydrochloride was left at the administration site at 61% for the first day after the administration, at 39% for the third day and at 8% for the fifth day.

In contrast thereto, with the ropivacaine hydrochloride-containing preparation prepared according to the existing method of Comparative Example C1, the ropivacaine hydrochloride was left at the administration site at 52% for the first day after the administration, at 22% for the third day and at 8% for the fifth day.

In view of the above, it was revealed that when comparing the ropivacaine hydrochloride-containing preparation prepared by the existing method with the ropivacaine hydrochloride-containing, controlled-release preparation of Example 2, the illustrative embodiment was able to release the local anesthetic persistently at the administration site and had the long-term releasability on clinical basis while keeping an adequate drug concentration.

Analgesic Effect of Local Anesthetic-Containing Controlled-Release Preparations at the Operative Wound Area Postoperative Pain Model of Rats (Foot Sole Pain Model of Rats)

A pentobarbital sodium injection (Nembutal injection, made by Sumitomo Dainippon Pharma Co., Ltd.) (0.3 mL) was intraperitoneally administered to male Wistar rats for anesthesia. Thereafter, a skin incision was made with a No. 11 scalpel blade (made by FEATHER Safety Razor Co., Ltd.) longitudinally at a position of 5 mm from the heel of the left foot bottom. The plantaris muscle was taken out from the incision site, followed by longitudinal incision. Subsequently, the skin was subjected to a knotted suture with a 5-0 nylon thread by double stitches. Moreover, a DERMA-BOND was applied in a single layer thereonto so as not to permit the administered controlled-release preparation to leak. The rats after the DERMABOND had been well dried were provided as a postoperative pain model of rats.

Behavioral Studies on Animal Pain (Test Method)

Prior to operation, nine to ten hours after the operation and further in every day till after 14 days, the von Frey filament test was carried out. This test had for its purpose the evaluation of pain against non-nociceptive stimuli wherein filaments (von Frey hair) having different thicknesses capable of applying a predetermined pressure were in touch with measurement sites to provide pressure stimuli, followed by measurement of a pressure at which a withdrawal response was caused to occur, thereby obtaining a withdrawal threshold against mechanical stimuli. More particularly, using the von Frey hair set (commercial name: Touch-Test, made by North Coast Medical Inc.) requiring a given stress before bending, this was pressed against the operated site of rats vertically from beneath the mesh of a gauge wherein rats were accommodated, whereupon a stress (a withdrawal threshold against mechanical stimuli) was determined at the time when the rat raised paws in surprise.

1. Analgesic Effect of Bupivacaine Hydrochloride-Containing, Controlled-Release Preparation on Operative Wound Area The efficacy of the bupivacaine hydrochloride-containing, controlled-release preparation of an illustrative embodiment was assessed.

(1) Method

Twelve 14-week-old-male Wistar rats (body weights: 370 g to 390 g) were arbitrarily divided into two groups each consisting of six rats and including a group wherein the bupivacaine hydrochloride-containing, controlled-release preparation was administered after incision (administration group) and a sham operation group wherein only the incision was performed (control group). Using the postoperative pain model of rat set out above, the analgesic effect of the bupivacaine hydrochloride-containing, controlled-release preparation of Example 1 was evaluated according to the von Frey filament test.

For the administration group, the bupivacaine hydrochloride-containing, controlled-release preparation of Example 1 was injected into the vicinity of the plantaris muscles in a predetermined amount (0.6 mg/body as an amount of bupivacaine hydrochloride) by means of a 27 G injector (made by Terumo Corporation). For the control group, the incision was made without administration of the local anesthetic (pain reliever).

(2) Results

Figure 3:
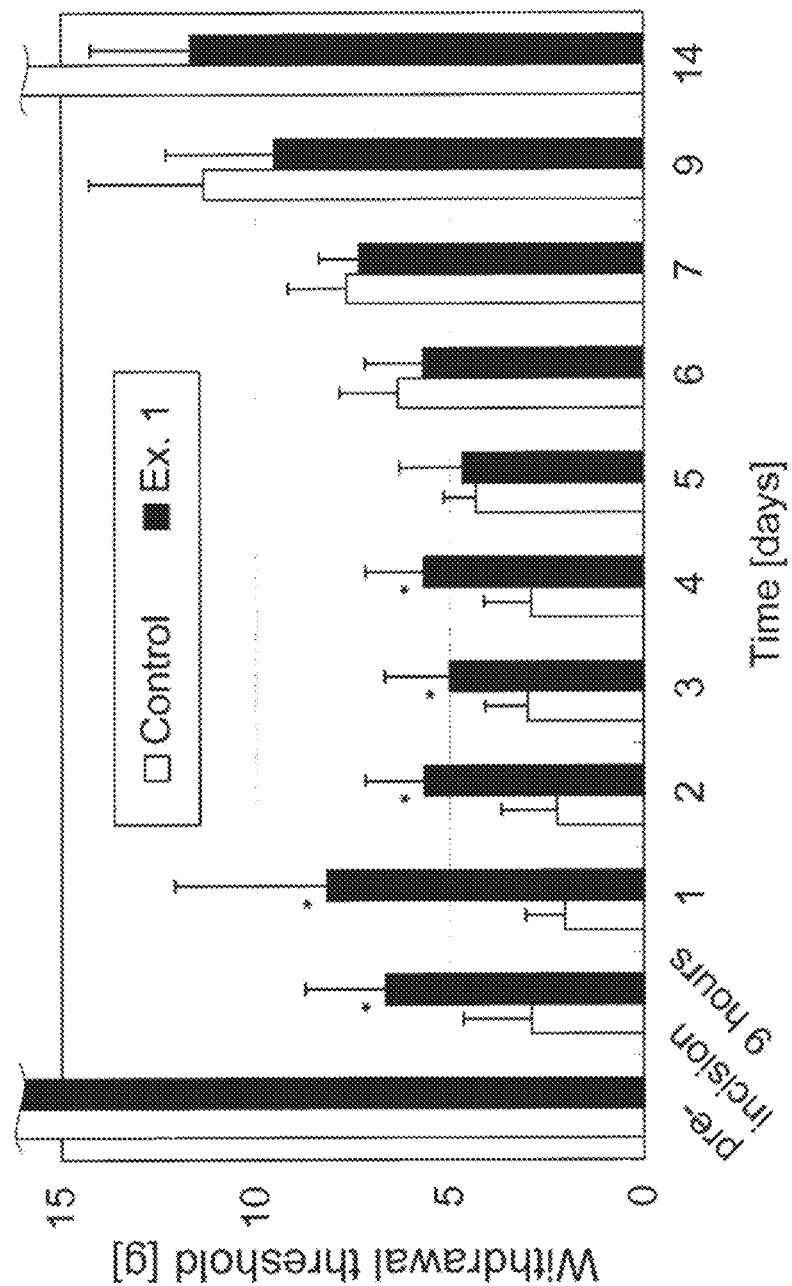
FIG. 3 is a graph showing a timewise change of a postoperative pain-relieving effect of a bupivacaine hydrochloride-containing, controlled-release preparation of Example 1.

The results of the von Frey filament test are shown in FIG. 3. In FIG. 3, "Ex. 1" means "administration group" wherein the bupivacaine hydrochloride-containing, controlled-release preparation of Example 1 was administered and "Control" means "control group." In FIG. 3, "Time (days)" of the abscissa means "postoperative elapses time (days)." In this regard, however, "Pre-incision" before one day means "before incision" and "9 hours" means "postoperative nine hours." "Withdrawal threshold [g]" of the ordinate means "withdrawal threshold (g) against mechanical stimuli." In FIG. 3, * (asterisk) in the graph means a significant difference relative to the control group (p value<0.05 when calculated in the t-test). It will be noted that all the withdrawal thresholds against mechanical stimuli prior to incision exceeded 15 g.

With the "control group" wherein no local anesthetic (pain reliever) was administered, the withdrawal threshold decreased remarkably over the case prior to incision, i.e., the pain continued over four days with a tendency toward restoration after the fifth and subsequent days.

With the "administration group" wherein the bupivacaine-containing, controlled-release preparation of Example 1, it was found that the threshold value significantly increased over the control group at all the times from postoperative nine hours to postoperative fourth day (p value<0.05).

The significant increase of the threshold value of the administration group over the control group means that the postoperative pain was significantly alleviated up to the postoperative fourth day, thus being noteworthy. With respect to postoperative fifth and subsequent days, since natural healing in the incision was in progress with a tendency toward restoration, intense postoperative pain was considered to continue to the fourth day. Accordingly, it was suggested that the analgesic duration of four days was adequate.

It is to be noted that as a result of the evaluation of the analgesic effect of bupivacaine hydrochloride itself (stock solution) using a similar postoperative pain model of rats, it was revealed that no increase of the threshold value was recognized from the postoperative first day and that no analgesic effect was obtained even at the postoperative first day. This is considered for the reason that the bupivacaine hydrochloride itself disappears immediately after administration, so that the alleviation time of postoperative pain is very short with no persistence.

From the foregoing, the bupivacaine hydrochloride-containing, controlled-release preparation of the illustrative embodiment was able to provide analgesic effect over four days when postoperatively administered once to an operative wound. This means that an adequate analgesic effect is obtained during a period of time when intense postoperative pain is felt. Thus, it is considered that when the bupivacaine hydrochloride-containing, controlled-release preparation of the illustrative embodiments is likely administered postoperatively to humans once at an operative wound, an analgesic effect can be obtained over an adequate period of time on a clinical basis.

2. Postoperative Analgesic Effect of Ropivacaine Hydrochloride-Containing, Controlled-Release Preparation (1)

The efficacy of the ropivacaine hydrochloride-containing, controlled-release preparation of an illustrative embodiment was evaluated.

(1) Method

Twelve ten-week-old-male Wistar rats (body weights: 290 g to 300 g) were arbitrarily divided into two groups, each consisting of six rats, including a group wherein a ropivacaine hydrochloride-containing, controlled-release preparation was administered after incision (administration group) and a sham operation group wherein only the incision was performed (control group). Using the postoperative pain model of rat set out before, the analgesic effect of the ropivacaine hydrochloride-containing, controlled-release preparation of Example 2 was evaluated, in a manner as stated above, according to the von Frey filament test.

For the administration group, the ropivacaine hydrochloride-containing, controlled-release preparation of Example 2 was injected into the vicinity of the plantaris muscles of the respective rats in a predetermined amount (0.5 mg/body as an amount of ropivacaine hydrochloride) by means of a 27 G injector (made by Terumo Corporation). For the control group, the incision was made without administration of the local anesthetic (pain reliever).

(2) Results

Figure 4:
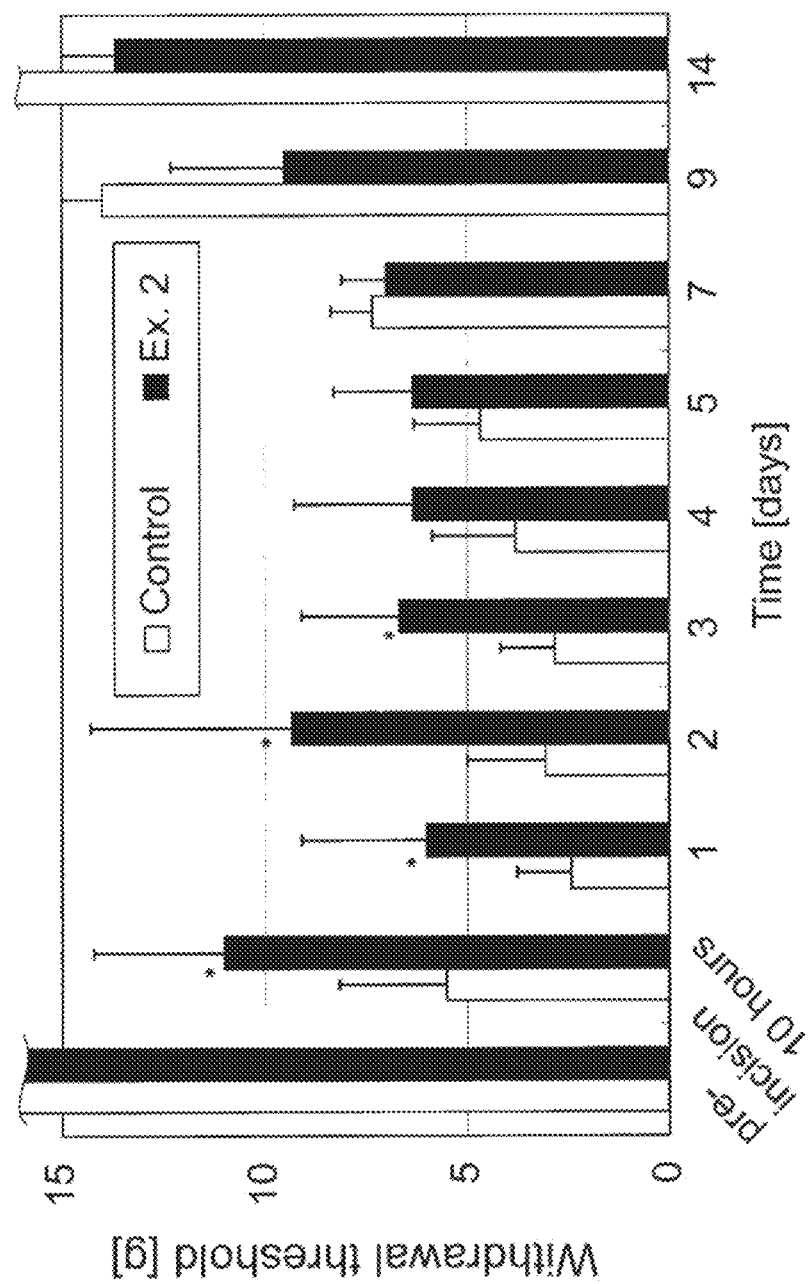
FIG. 4 is a graph showing a timewise change of a postoperative analgesic effect of a ropivacaine hydrochloride-containing, controlled-release preparation of Example 2.

The results of the von Frey filament test are shown in FIG. 4. In FIG. 4, "Ex. 2" means "administration group" wherein the ropivacaine hydrochloride-containing, controlled-release preparation of Example 2 was administered and "Control" means "control group." In FIG. 4, "Time (days)" of the abscissa means "postoperative elapses time (days)." In this regard, however, "Pre-incision" before one day means "before incision" and "10 hours" means "postoperative ten hours." "Withdrawal threshold [g]" of the ordinate means "withdrawal threshold (g) against mechanical stimuli." In FIG. 4, * (asterisk) in the graph means a significant difference relative to the control group (p value<0.05 when calculated in the t-test). It will be noted that all the withdrawal thresholds against mechanical stimuli prior to incision exceeded 15 g.

With the "control group" wherein no local anesthetic (pain reliever) was administered, the withdrawal threshold decreased remarkably over the case prior to incision, i.e., the pain continued over four days with a tendency toward restoration after the fifth and subsequent days.

With the "administration group" wherein the ropivacaine hydrochloride-containing, controlled-release preparation of Example 2, it was recognized that the threshold values significantly increased over the control group at all the times from postoperative ten hours to postoperative third day (p value<0.05). Accordingly, it was revealed that with the administration group, the postoperative pain was significantly alleviated till the postoperative third day.

It should be noted that as a result of the evaluation of the analgesic effect of ropivacaine hydrochloride itself (stock solution) using a similar postoperative pain model of rat, it was revealed that no increase of the threshold value was recognized from the postoperative first day and that no analgesic effect was obtained even at the postoperative first day. This is considered for the reason that the ropivacaine hydrochloride itself disappears immediately after administration like the bupivacaine hydrochloride, so that the alleviation time of postoperative pain is very short with no persistence.

From the foregoing, when postoperatively administered once to an operative wound, the ropivacaine hydrochloride-containing, controlled-release preparation of the illustrative embodiment was able to provide an analgesic effect over three to four days like the bupivacaine hydrochloride-containing, controlled-release preparation. Thus, it is considered that when the long-lasting, controlled-release local anesthetic preparation is administered postoperatively to humans once at an operative wound, an analgesic effect can be obtained over an adequate period of time on a clinical basis.

3. Postoperative Analgesic Effect of Ropivacaine Hydrochloride-Containing, Controlled-Release Preparations (2)

The efficacies of the ropivacaine hydrochloride-containing, controlled-release preparations of illustrative embodiments were compared with one another.

(1) Method

Twenty four ten-week-old-male Wistar rats (body weight: 280 g to 300 g) were arbitrarily divided into four groups, each consisting of six rats, including a group (administration group 1) wherein the ropivacaine hydrochloride-containing, controlled-release preparation of Example 3 was administered after incision, a group (administration group 2) wherein the ropivacaine hydrochloride-containing, controlled-release preparation of Example 4 was administered after incision, a group (administration group 3) wherein the ropivacaine hydrochloride-containing, controlled-release preparation of Example 5 was administered after incision, and a sham operation group (control group) wherein only the incision was performed. Using the postoperative pain model of rat set out before, the analgesic effect of the ropivacaine hydrochloride-containing, controlled-release preparations of Examples 3 to 5 was evaluated, in a manner as stated before, according to the von Frey filament test.

For the administration groups 1 to 3, each of the ropivacaine hydrochloride-containing, controlled-release preparations of Examples 3 to 5 was injected into the vicinity of the plantaris muscle of the respective rats in a predetermined amount (0.54 mg/body as an amount of ropivacaine hydrochloride) by means of a 27 G injector (made by Terumo Corporation). For the control group, the incision was made without administration of a local anesthetic (pain reliever).

(2) Results

Figure 5:
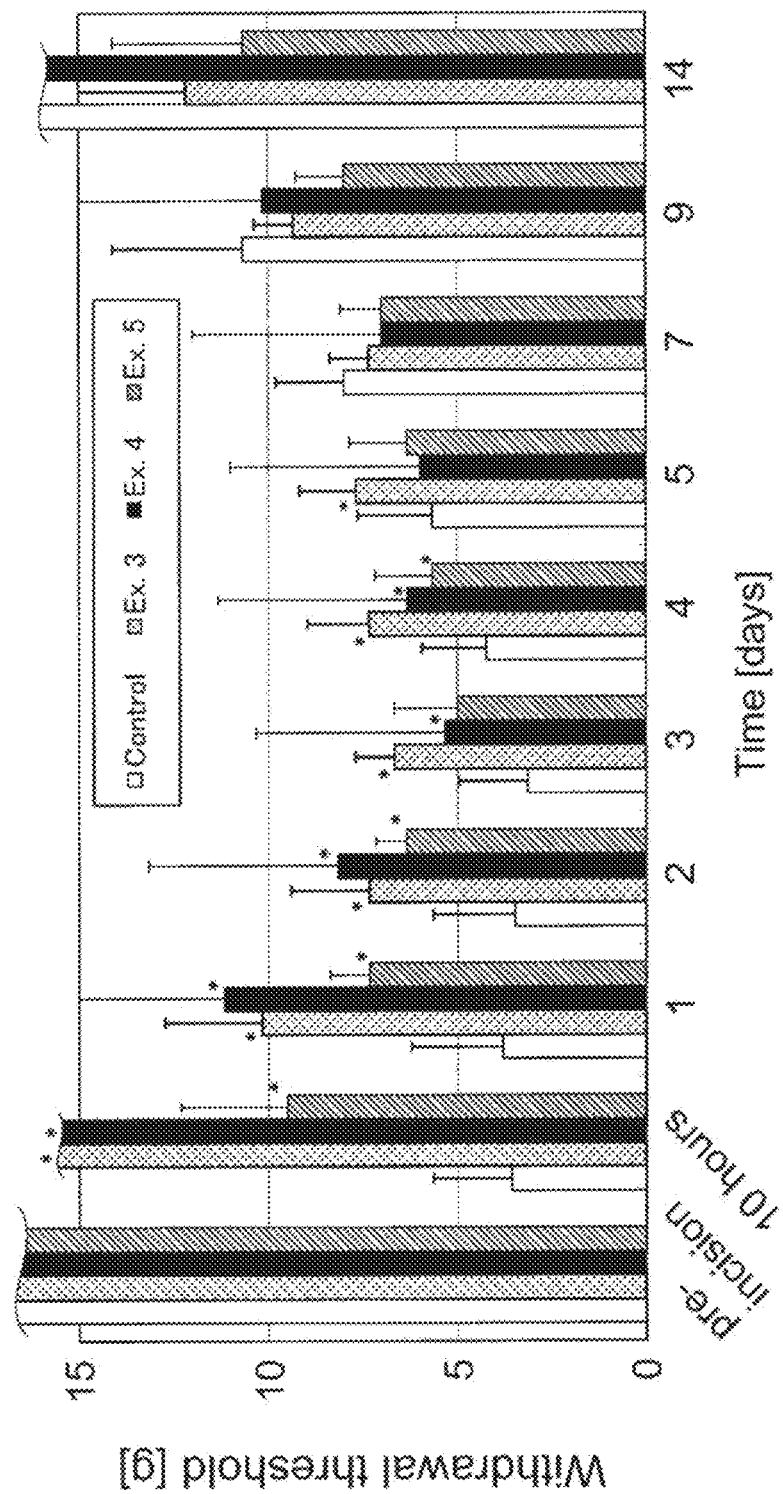
FIG. 5 is a graph showing a timewise change of a postoperative analgesic effect of the respective ropivacaine hydrochloride-containing, controlled-release preparations of Examples 3 to 5.

The results of the von Frey filament test are shown in FIG. 5. In FIG. 5, "Ex. 3," "Ex. 4" and "Ex. 5," respectively, mean "administration group 1" wherein the ropivacaine hydrochloride-containing, controlled-release preparation of Example 3 was administered, "administration group 2" wherein the ropivacaine hydrochloride-containing, controlled-release preparation of Example 4 was administered and "administration group 3" wherein the ropivacaine hydrochloride-containing, controlled-release preparation of Example 5 was administered. In FIG. 5, "Time (days)" of the abscissa means "postoperative elapses time (days)." In this regard, however, "Pre-incision" before one day means "before incision" and "10 hours" means "postoperative ten hours." "Withdrawal threshold [g]" of the ordinate means "withdrawal threshold (g) against mechanical stimuli." In FIG. 5, * (asterisk) in the graph means a significant difference relative to the control group (p value<0.05 when calculated in the t-test). It will be noted that all the withdrawal thresholds against mechanical stimuli prior to incision exceeded 15 g.

With the "control group" wherein no local anesthetic (pain reliever) was administered, the withdrawal threshold decreased remarkably over the case prior to incision, i.e., the pain continued over four days with a tendency toward restoration after the fifth and subsequent days. On the other hand, the "administration group 1" wherein the ropivacaine hydrochloride-containing, controlled-release preparation of Example 3 was administered, "administration group 2" wherein the ropivacaine hydrochloride-containing, controlled-release preparation of Example 4 was administered and "administration group 3" wherein the ropivacaine hydrochloride-containing, controlled-release preparation of Example 5 was administered were recognized to have significant increases of threshold value over the control group at all the times from postoperative ten hours to postoperative fourth day (p value<0.05). Accordingly, it was revealed that with the ropivacaine hydrochloride-containing, controlled-release preparations of Examples 3 to 5, the postoperative pain was significantly alleviated till the postoperative fifth day. Moreover, variations in threshold value of the administration groups showed a similar tendency.

4. Postoperative Analgesic Effect of Ropivacaine Hydrochloride-Containing, Controlled-Release Preparations (3)

The efficacies between the ropivacaine hydrochloride-containing, controlled-release preparation of an illustrative embodiment and a ropivacaine hydrochloride-containing preparation prepared by an existing method (extruder method) were compared.

(1) Method

Eighteen ten-week-old-male Wistar rats (body weight: 290 g to 320 g) were arbitrarily divided into three groups, each consisting of six rats, including a group (administration group 1) wherein the ropivacaine hydrochloride-containing preparation of Example 6 was administered after incision, a group (administration group 2) wherein the ropivacaine hydrochloride-containing, controlled-release preparation of Comparative Example C2 was administered after incision, and a sham operation group (control group) wherein only the incision was performed. Using the postoperative pain model of the rat set out before, the analgesic effect of the ropivacaine hydrochloride-containing, controlled-release preparation of Example 6 and the analgesic effect of the ropivacaine hydrochloride-containing preparation of Comparative Example C2 were evaluated according to the von Frey filament test as set out before.

Each of the ropivacaine hydrochloride-containing, controlled-release preparation of Example 6 for the administration group 1 and the ropivacaine hydrochloride-containing preparation of Comparative Example C2 for the administration group 2 was injected into the vicinity of the plantaris muscle in a predetermined amount (0.55 mg/body as an amount of ropivacaine hydrochloride) by means of a 27 G injector (made by Terumo Corporation). For the control group, the incision was made without administration of a local anesthetic (pain reliever).

(2) Results

Figure 6:
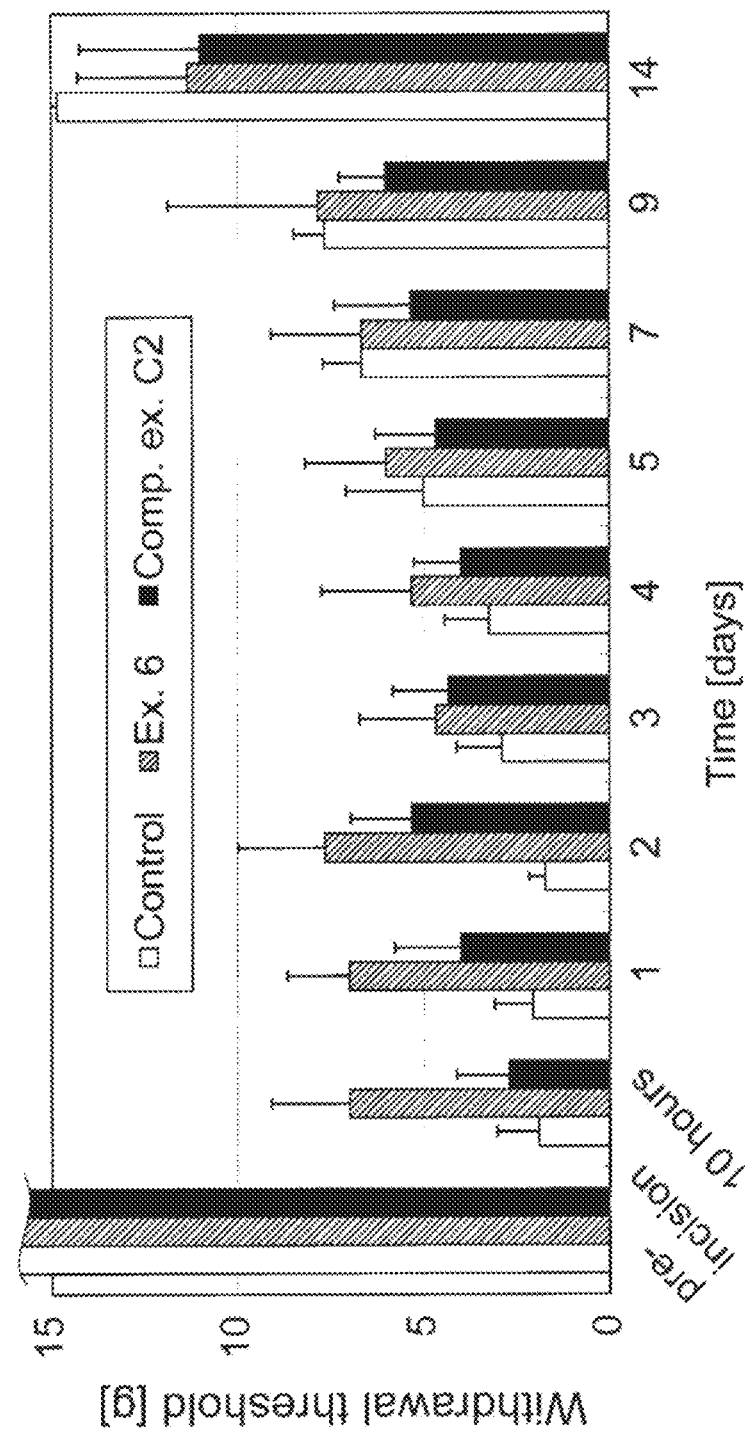
FIG. 6 is a graph showing a timewise change of a postoperative analgesic effect of a ropivacaine hydrochloride-containing, controlled-release preparation of Example 6 and a ropivacaine hydrochloride-containing preparation of Comparative Example C2.

The results of the von Frey filament test are shown in FIG. 6. In FIG. 6, "Ex. 6" means "administration group 1" wherein the ropivacaine hydrochloride-containing, controlled-release preparation of Example 6 was administered, "Comp. ex. C2" means the "administration group 2" wherein the ropivacaine hydrochloride-containing preparation of Comparative Example C2 was administered, and "Control" means the "control group." In FIG. 6, "Time (days)" of the abscissa means "postoperative elapses time (days)." In this regard, however, "Pre-incision" before one day means "before incision" and "10 hours" means "postoperative ten hours." "Withdrawal threshold [g]" of the ordinate means "withdrawal threshold (g) against mechanical stimuli." It will be noted that all the withdrawal thresholds against mechanical stimuli prior to incision exceeded 15 g.

With the "control group" wherein no local anesthetic (pain reliever) was administered, the withdrawal threshold decreased remarkably over the case prior to incision, i.e., the pain continued over four days with a tendency toward restoration after the fifth and subsequent days.

The "administration group 1," in which the ropivacaine hydrochloride-containing, controlled-release preparation of Example 6 was administered, was recognized to have a significant increase of threshold value over the control group at all the times from postoperative ten hours to postoperative second day (p value<0.05 when calculated in the t-test).

The ropivacaine hydrochloride-containing preparation of Comparative Example C2 prepared according to the existing method (extruder method) had a predominantly increased threshold value over the control group at the postoperative second day (p value<0.05) but with the result that the analgesic effect was inferior to that of the administration group 1 as a whole and the persistence of the analgesic effect was not adequate.

The difference in the postoperative analgesic effect between the ropivacaine hydrochloride-containing, controlled-release preparation of Example 6 and the ropivacaine hydrochloride-containing preparation of Comparative Example C2 is considered such that the ropivacaine hydrochloride-containing preparation of Comparative Example C2 allows rapid release of ropivacaine hydrochloride, so that the persistence of the postoperative analgesic effect is not adequately shown.

Analgesic Effect of Local Anesthetic-Containing, Controlled-Release Preparations on a Sciatic Nerve Block Model Model of Rat Plantaris Muscle Incision (Double-Stitch Suture)+Affected Sciatic Nerve Block A pentobarbital sodium injection (Nembutal injection, made by Sumitomo Dainippon Pharma Co., Ltd.) (0.3 mL) was intraperitoneally administered to male Wistar rats for anesthesia, followed by shaving off the hair on the left femoral area. In the abdominal position, the skin on the femur was incised, after sterilization, by 1 cm by means of a No. 11 scalpel blade (made by FEATHER Safety Razor Co., Ltd.), followed by separation of the subcutaneous layer to permit the biceps femoris muscle to be exposed. The groove between the biceps femoris muscles was recognized, and the fascia was incised to bluntly separate the head muscles from each other thereby recognizing the white sciatic nerve. The sciatic nerve was humanely held, under which a local anesthetic-containing, controlled-release preparation was locally injected into the sciatic nerve adventitia, followed by suture closure of the skin of the femoral area by double stitching with 5-0 nylon without suturing of the fascia. Thereafter, the foot sole and plantaris muscle at the same side were subsequently incised and subjected to double-stitching with 5-0 nylon to provide a model of rat plantaris muscle incision (double-stitch suture)+affected sciatic nerve block.

1. Analgesic Effect of a Ropivacaine Hydrochloride-Containing, Controlled-Release Preparation on the Sciatic Nerve Block Model The efficacies of the ropivacaine hydrochloride-containing, controlled-release preparation of an illustrative embodiment and Exparel that is a commercially available bupivacaine hydrochloride-containing liposome preparation were evaluated.

(1) Method

Eighteen 14-week-old-male Wistar rats (body weight: 370 g to 390 g) were arbitrarily divided into three groups, each consisting of six rats, including (administration group 1) of the exposure of the sciatic nerve (wherein 24 µL of the ropivacaine hydrochloride-containing, controlled-release preparation of Example 7 was locally injected into the epineurium)+the incision of the plantaris muscle (double-stitch suture), (administration group 2) of the exposure of the sciatic nerve (wherein 40 µL of Exparel of Comparative Example C3 was locally injected into the epineurium)+the incision of the plantaris muscle (double-stitch suture)), and (control group) of the exposure of the sciatic nerve (wherein 40 µL of a physiological saline solution was locally injected into the epineurium)+the incision of the plantaris muscle (double-stitch suture). Using the model of the rat plantaris muscle incision (double-stitch suture)+the affected sciatic nerve block, the analgesic effects of the ropivacaine hydrochloride-containing, controlled-release preparation of Example 7 and Exparel of Comparative Example C3 were evaluated according to the von Frey filament test as set out before.

The ropivacaine hydrochloride-containing, controlled-release preparation of Example 7 for the administration group 1 and Exparel of Comparative Example C3 for the administration group 2 were locally injected into the epineurium in a predetermined amount (0.6 mg/body as an amount of ropivacaine hydrochloride or bupivacaine hydrochloride) by means of a 27 G injector (made by Terumo Corporation). For the control group, the incision was made without administration of a local anesthetic (pain reliever).

(2) Results

Figure 7:
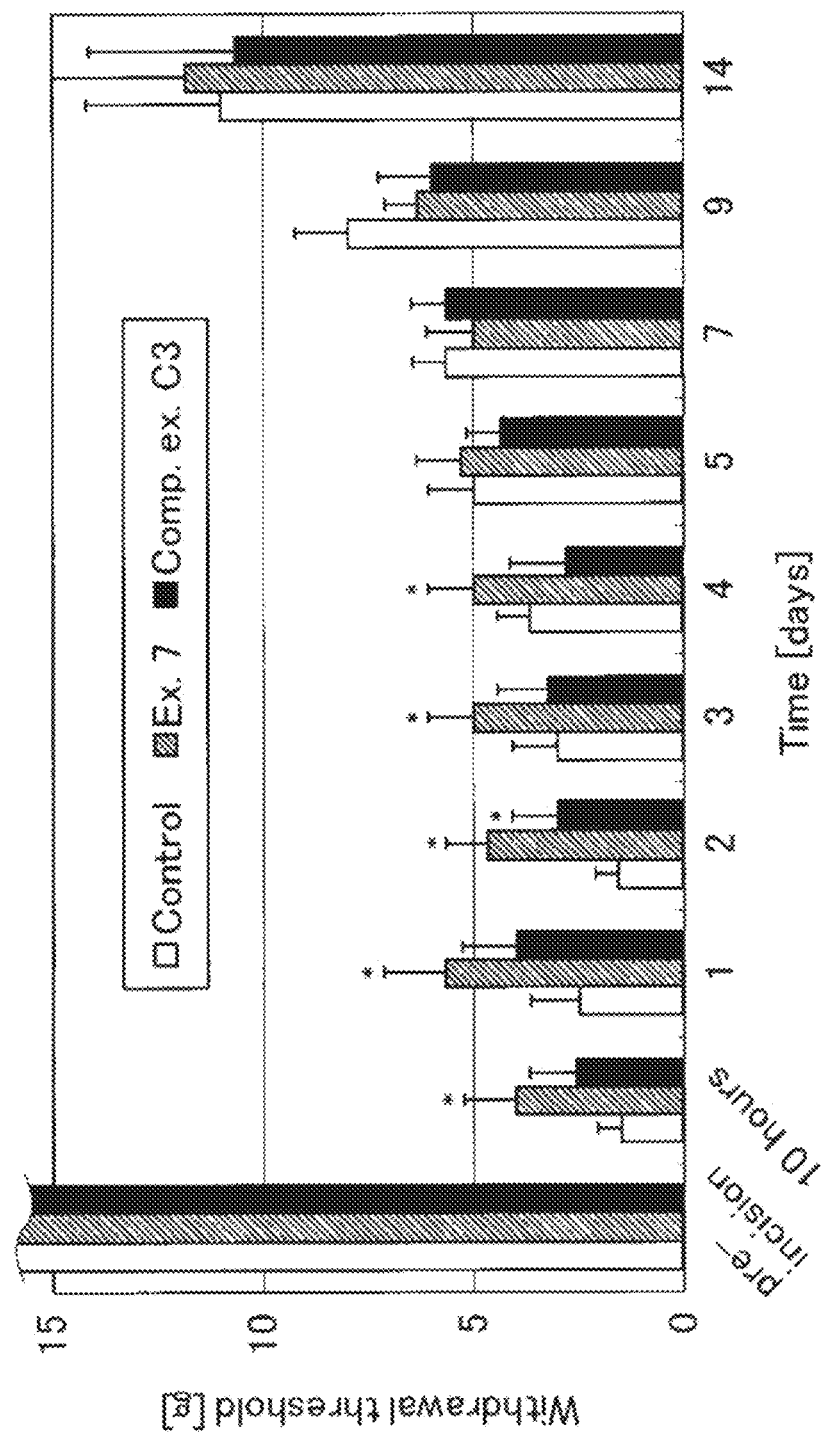
FIG. 7 is a graph showing a timewise change of a postoperative analgesic effect of a ropivacaine hydrochloride-containing, controlled-release preparation of Example 7 and a ropivacaine hydrochloride-containing liposome preparation of Comparative Example C3.

The results of the von Frey filament test are shown in FIG. 7. In FIG. 7, "Ex. 7" means "administration group 1" wherein the ropivacaine hydrochloride-containing, controlled-release preparation of Example 7 was administered, "Comp. ex. C3" means the "administration group 2" wherein Exparel of Comparative Example C3 was administered, and "Control" means "control group." In FIG. 7, "Time (days)" of the abscissa means "postoperative elapses time (days)." In this regard, however, "Pre-incision" before one day means "before incision" and "10 hours" means "postoperative ten hours." "Withdrawal threshold [g]" of the ordinate means "withdrawal threshold (g) against mechanical stimuli." * (Asterisk) in the graph means a significant difference relative to the control group (p value<0.05 when calculated in the t-test). It will be noted that all the withdrawal thresholds against mechanical stimuli prior to incision exceeded 15 g.

With the "control group" wherein no local anesthetic (pain reliever) was administered, the withdrawal threshold decreased remarkably over the case prior to incision, i.e., the pain continued over four days with a tendency toward restoration after the fifth and subsequent days.

With the "administration group 1" wherein the ropivacaine hydrochloride-containing, controlled-release preparation of Example 7 was administered, a significant increase of the threshold value over the control group was recognized at all the times from postoperative ten hours to postoperative fourth day (p value<0.05). Accordingly, it was revealed that the ropivacaine hydrochloride-containing, controlled-release preparation of the illustrative embodiment was able to significantly alleviate the postoperative pain up to the postoperative fourth day in the model of affected sciatic nerve block.

With the "administration group 2" to which Exparel was administered, the analgesic effect was inferior to that of the administration group 1, resulting in the continuation of the analgesic effect only to the second day.

With the "administration group 1" wherein the ropivacaine hydrochloride-containing, controlled-release preparation of Example 7 was administered, it was recognized that the threshold value significantly increased from the postoperative ten hours till the postoperative fourth day when comparing with the "administration group 2" wherein Exparel was administered.

From the foregoing, it was demonstrated that, in the model of affected sciatic nerve block, the ropivacaine hydrochloride-containing, controlled-release preparation of the illustrative embodiment showed a significant analgesic effect over the postoperative four days, ensured a longer persistence than Exparel, and was significantly excellent in the analgesic effect.

Structure of Liposome Preparation

Figure 8:
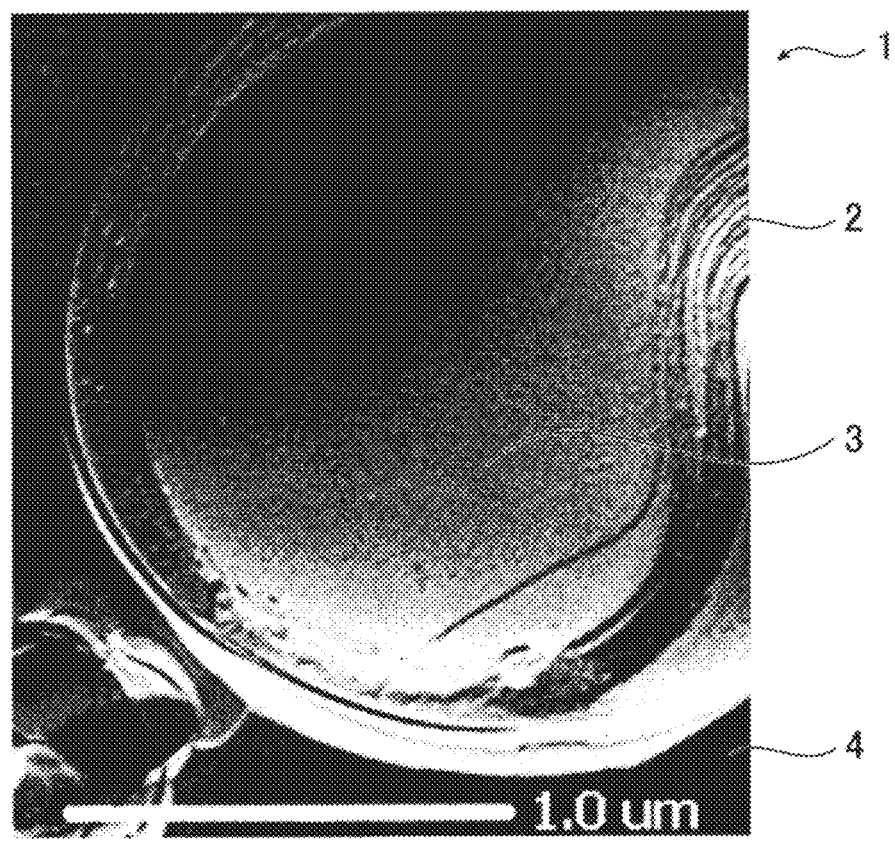
FIG. 8 is a view showing an illustrative liposome preparation used for a long-lasting, controlled-release local anesthetic preparation.

FIG. 8 is a photograph of a median section obtained by observing through a transmission electron microscope (TEM) a section of a liposome preparation obtained after introduction of a drug in a liposome composition prepared in the similar way as the liposome composition used for a long-lasting, controlled-release local anesthetic liposome preparation of an illustrative embodiment.

The liposome preparation shown in FIG. 8 is divided substantially at the center thereof. It will be seen that a liposome 1 indicated in FIG. 8 includes a structure having one homogeneous internal aqueous phase 3 having a liposome membrane 2 formed of a plurality of lipid bilayer membranes.

The liposome composition indicated in FIG. 8 after introduction of the drug used for the photography was prepared according to the similar way as for the liposome composition used for the long-lasting, controlled-release local anesthetic preparation of the illustrative embodiments. Thus, the long-lasting, controlled-release local anesthetic preparation of the illustrative embodiments had a similar configuration as the liposome of FIG. 8.

The liposome composition after the introduction of a drug used for the photography in FIG. 8 was prepared in the following way.

(1) Preparation of Empty Liposomes

HSPC (2.82 g) and Chol (1.18 g) were each weighed, to which absolute ethanol (2 mL) was added so that a lipid concentration in the absolute ethanol was at 200 w/v %, followed by dissolution under heating at about 70° C. to prepare a lipid ethanol solution.

An internal aqueous phase solution (150 mM ammonium sulfate aqueous solution) (8 mL) serving as a first aqueous phase was added to the lipid ethanol solution (2 mL) prepared in this manner at such a ratio by volume of the internal aqueous phase to the lipid ethanol solution so that the internal aqueous phase/lipid ethanol solution=4/1 (v/v), followed by heating under agitation at a given speed of rotation for about ten minutes to prepare empty liposomes. The liposomes obtained after completion of the heating were quickly cooled with ice.

(2) Formation of pH Gradient

The empty liposomes after the ice cooling were subjected to external solution exchange by use of a centrifugal separator to form a pH gradient between the internal aqueous phase side/the external aqueous phase side of the liposomes.

The liposomes were dispersed in an about ten-fold the amount of a 20 mM HEPES/0.9% NaCl solution (with a pH of 7.5), followed by centrifugal separation at 1,230×g for 15 minutes to precipitate the empty liposomes. Thereafter, the supernatant was removed. Subsequently, a 20 mM HEPES/0.9% NaCl solution (with a pH of 7.5) was added for dispersion and subjected to centrifugal separation in a similar way. This was repeated three times.

Thereafter, a 20 mM HEPES/0.9% NaCl solution (with a pH of 7.5) was added so as to re-disperse the empty liposomes thereby forming a pH gradient.

(3) Introduction of a Local Anesthetic by Use of the pH Gradient

The amounts of HSPC and cholesterol in the empty liposomes after the formation of pH gradient were quantitatively determined to obtain a total lipid concentration. Based on the total lipid concentration calculated in this manner, an amount of donepezil hydrochloride was so calculated that a ratio of donepezil hydrochloride (DNP, molecular weight: 415.95)/total lipid (mol/mol) was set at 0.16. A required amount of DNP was weighed, followed by adding RO water to prepare 20 mg/mL of a DNP solution (drug solution).

A given amount of the DNP solution heated to 65° C. beforehand was added to the liposome dispersion liquid heated to 65° C., followed by heating under agitation at 65° C. for 60 minutes to introduce the drug. The liposomes after the introduction of the drug were quickly cooled with ice.

(4) Removal of Unencapsulated Drug

An external aqueous phase solution (20 mM HEPES/0.9% NaCl solution (with a pH of 7.5)) was added so as to disperse the liposomes after the drug introduction, followed by centrifugal separation at 1,230×g for 15 minutes to precipitate the liposomes. Thereafter, the supernatant was removed. Subsequently, a 20 mM HEPES/0.9% NaCl solution (with a pH of 7.5) was added for dispersion and subjected to centrifugal separation in a similar way. This was repeated three times to remove the unencapsulated drug.

The detailed description above describes a long-lasting, controlled-release local anesthetic liposome preparation. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

DESCRIPTION OF REFERENCE NUMERALS

1: Liposome
2: Liposome membrane
3: Internal aqueous phase
4: External aqueous phase

What is claimed is:

1. A long-lasting, controlled-release local anesthetic liposome preparation, which is prepared by: providing a liposome composition obtained by mixing, in a water-miscible organic solvent, a first aqueous phase solution with a water-miscible organic solution, in which a phospholipid and cholesterol are contained at a total concentration of 100 w/v % to 200 w/v %, at a ratio by volume of 3/1 to 12/1 in terms of the unit volume to the water-miscible organic solution thereby obtaining an emulsion wherein a total concentration of the phospholipid and cholesterol in the mixed phase is at 15 w/v % to 50 w/v %, followed by subjecting the emulsion to external solution exchange with a second aqueous phase solution to obtain a liposome composition wherein an ion gradient is formed between an internal-region aqueous phase of a liposome membrane made of the first aqueous phase solution and an external-region aqueous phase of the liposome membrane made of the second aqueous phase solution; and encapsulating a local anesthetic in the internal-region aqueous phase of empty liposomes formed from the phospholipid and cholesterol, wherein the internal-region aqueous phase is in a multilayer membrane having a layered structure of at least 12 layers.

2. The long-lasting, controlled-release local anesthetic liposome preparation as defined in claim 1, wherein the ion gradient is a proton gradient and a pH of the internal-region aqueous phase of the liposome is lower than a pH of the external-region aqueous phase of the liposome.

3. The long-lasting, controlled-release local anesthetic liposome preparation as defined in claim 1, wherein the local anesthetic is retained in the liposome at not less than 0.08 (mol)/total lipids (mol).

4. The long-lasting, controlled-release local anesthetic liposome preparation as defined in claim 1, wherein the liposome has an average particle diameter of not less than 1 μm.

5. The long-lasting, controlled-release local anesthetic liposome preparation as defined in claim 1, which is used for delivery at an operative wound area and/or an adjacent site thereof, or a nerve periphery transmitting pain according to at least one of methods selected from the group consisting of injection, infiltration and embedment.

6. The long-lasting, controlled-release local anesthetic liposome preparation as defined in claim 1, which is administered in at least one manner selected from the group consisting of subcutaneous, myofascial and intramuscular manners over an operative wound area and/or an adjacent site thereof, or a nerve periphery transmitting pain.

7. The long-lasting, controlled-release local anesthetic liposome preparation as defined in claim 1, which brings about an analgesic duration for not less than three days after administration.

8. The long-lasting, controlled-release local anesthetic liposome preparation as defined in claim 1, wherein the local anesthetic is at least one amino amide-type anesthetic selected from the group consisting of bupivacaine, ropivacaine, levobupivacaine, lidocaine, mepivacaine, prilocaine and salts thereof.

9. The long-lasting, controlled-release local anesthetic liposome preparation as defined in claim 1, which is able to be administered by an injector having an injection needle having at least one gauge size selected from among 27 gauge to 34 gauge.

10. A kit for a long-lasting, controlled-release local anesthetic liposome preparation, which comprises the long-lasting, controlled-release local anesthetic liposome preparation defined in claim 9 and an injector having an injection needle having at least one gauge size selected from among 27 gauge to 34 gauge.

11. A method for locally anesthetizing a human, the method comprising the step of administering, to a human, a long-lasting, controlled-release local anesthetic liposome preparation defined in claim 1.

12. A method for preparing a long-lasting, controlled-release local anesthetic liposome preparation comprising: preparing a liposome composition by mixing, in a water-miscible organic solvent, a first aqueous phase solution with a water-miscible organic solution, in which a phospholipid and cholesterol are contained at a total concentration of 100 w/v % to 200 w/v %, at a ratio by volume of 3/1 to 12/1 in terms of the unit volume to the water-miscible organic solution thereby obtaining an emulsion wherein a total concentration of the phospholipid and cholesterol in the mixed phase is at 15 w/v % to 50 w/v %; subjecting the emulsion to external solution exchange with a second aqueous phase solution to obtain the liposome composition wherein an ion gradient is formed between an internal-region aqueous phase of a liposome membrane made of the first aqueous phase solution and an external-region aqueous phase of the liposome membrane made of the second aqueous phase solution; and encapsulating a local anesthetic in the internal-region aqueous phase of empty liposomes formed from the phospholipid and cholesterol to provide the long-lasting, controlled-release local anesthetic liposome preparation, wherein the internal-region aqueous phase is in a multilayer membrane having a layered structure of at least 12 layers.

13. The method as defined in claim 12, wherein the ion gradient is a proton gradient and a pH of the internal-region aqueous phase of the liposome is lower than a pH of the external-region aqueous phase of the liposome.

14. The method as defined in claim 12, wherein the local anesthetic is retained in the liposome at not less than 0.08 (mol)/total lipids (mol).

15. The method as defined in claim 12, wherein the liposome has an average particle diameter of not less than 1 μm.

16. The method as defined in claim 12, wherein the local anesthetic is at least one amino amide-type anesthetic selected from the group consisting of bupivacaine, ropivacaine, levobupivacaine, lidocaine, mepivacaine, prilocaine and salts thereof.

17. A method of delivering a long-lasting, controlled-release local anesthetic liposome preparation to an operative wound area and/or an adjacent site thereof, or a nerve periphery transmitting pain,
  wherein said method of delivering is selected from the group consisting of injecting, infiltrating and embedding,
  wherein said long-lasting, controlled-release local anesthetic liposome preparation is prepared by: providing a liposome composition obtained by mixing, in a water-miscible organic solvent, a first aqueous phase solution with a water-miscible organic solution, in which a phospholipid and cholesterol are contained at a total concentration of 100 w/v % to 200 w/v %, at a ratio by volume of 3/1 to 12/1 in terms of the unit volume to the water-miscible organic solution thereby obtaining an emulsion wherein a total concentration of the phospholipid and cholesterol in the mixed phase is at 15 w/v % to 50 w/v %, followed by subjecting the emulsion to external solution exchange with a second aqueous phase solution to obtain a liposome composition wherein an ion gradient is formed between an internal-region aqueous phase of a liposome membrane made of the first aqueous phase solution and an external-region aqueous phase of the liposome membrane made of the second aqueous phase solution; and encapsulating a local anesthetic in the internal-region aqueous phase of empty liposomes formed from the phospholipid and cholesterol, wherein the internal-region aqueous phase is in a multilayer membrane having a layered structure of at least 12 layers,
  wherein the operative wound area comprises an operative wound site associated with gastrectomy, hepatectomy, appendectomy, Caesarean operation, cholecystectomy, hysterectomy, colectomy, prostatectomy, discectomy, oophorectomy, orthopedic operation, coronary artery bypass graft surgery, or debridement,
  wherein the long-lasting, controlled-release local anesthetic liposome preparation is administered to at least one site selected from the group consisting of subcutaneous, peritoneal, myofascial and intramuscular sites, and
  wherein said method of delivering comprises steps of:
    closing fascia of an operative wound area having an incision site to be sutured,
    administering the long-lasting, controlled-release local anesthetic preparation along an operative wound to the fascia and/or muscle therebeneath with an injection needle at a plurality of portions, and
    totally closing skin after the administering to the fascia and/or the muscle.

18. The method as defined in claim 17, wherein the long-lasting, controlled-release local anesthetic liposome preparation is delivered in a manner selected from the group consisting of subcutaneous, myofascial and intramuscular.

19. The method as defined in claim 17, further comprising, after the closing with suturation, a step of uniformly, subcutaneously administering the long-lasting, controlled-release local anesthetic liposome preparation at a position in the vicinity of a suture thread along a sutured incision site and a position surrounding the incision site at a plurality of portions.

20. The method as defined in claim 17, wherein the injection needle is stabbed vertically or inclinedly relative to the skin so as to permit a tip of the injection needle to come close to the sutured incision site.

21. The method as defined in claim 17, further comprising, after the closing with suturation, a step of confirming, on the skin, a bloated feeling under injected skin.

22. The method as defined in claim 17, wherein, after the administering, postoperative pain in a postoperative pain model is alleviated for 4 days determined by a von Frey filament test.

23. The method as defined in claim 17, wherein, after the administering, postoperative pain in a sciatic nerve block model is alleviated for 4 days determined by a von Frey filament test.

* * * * *